US007704724B1

(12) United States Patent
Fry et al.

(10) Patent No.: US 7,704,724 B1

(45) Date of Patent: Apr. 27, 2010

(54) CATALYTIC BUFFERING SYSTEMS

(75) Inventors: Ilona J. Fry, Edgewood, MD (US); Joseph J. DeFrank, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 763 days.

(21) Appl. No.: 11/345,679

(22) Filed: Jan. 26, 2006

(51) Int. Cl.

| | |
|---|---|
| ***C12N 15/55*** | (2006.01) |
| ***C12N 1/21*** | (2006.01) |
| *C12N 9/80* | (2006.01) |

(52) U.S. Cl. ................. 435/252.3; 435/320.1; 435/228; 536/23.2

(58) Field of Classification Search ....................... None
See application file for complete search history.

(56) References Cited

U.S. PATENT DOCUMENTS

| | | | | |
|---|---|---|---|---|
| 5,928,927 | A * | 7/1999 | Cheng et al. | 435/196 |
| 6,054,310 | A * | 4/2000 | Kim et al. | 435/252.4 |
| 6,080,566 | A * | 6/2000 | Cheng et al. | 435/196 |
| 6,469,145 | B1 * | 10/2002 | Rastogi et al. | 530/412 |
| 6,599,733 | B1 * | 7/2003 | Fry et al. | 435/252.4 |
| 7,001,758 | B1 * | 2/2006 | Fry et al. | 435/262.5 |
| 7,229,819 | B1 * | 6/2007 | Cheng et al. | 435/264 |

OTHER PUBLICATIONS

Mobley H. L. et al., Microbial Ureases: Significance, Regulation, and Molecular Characterization, Microbiol. Review, 1989, 53, 85-108.*

Park I.S. et al. Site-directed mutagenesis of *Klebsiella aerogenes* urease: Identification of histidine residues that appear to function in nikel ligation, substrate binding, and catalysis, Prot. Sci., 1993, 2, 1034-1041.*

Todd M. J. et al., Fluoride Inhibition of *Klebsiella aerogenes* Urease: Mechanistic Implications of a Pseudo-uncompetetive, Slow-Binding inhibitor, Biochem., 2000, 39, 5389-5396.*

I.J. Fry et al. "Enhanced Peroxide Resistance of In Vitro Mutagenized Fluorideresistant Klebsiella pneumoniae Ureases for Catalytic Buffering of Agent Decontamination Reactions.", NTIS Order No. ADA449582/XAB (Nov. 17, 2004).*

* cited by examiner

*Primary Examiner*—Rebecca Prouty
(74) *Attorney, Agent, or Firm*—Ulysses John Biffoni

(57) ABSTRACT

Compositions and methods for catalytic buffering of enzymatic decontamination reactions are provided. Enzymatic decontamination of organophosphorus or organohalogen compounds generates acidic reaction products that precipitously reduce the pH of the medium, thus impairing activity of the decontaminating enzymes. Catalytic buffering, that is, the use of an enzyme to produce ions from a substrate to modulate pH, can provide effective pH control. The compositions provided here include urease enzymes with mutations in the alpha subunit of the urease holoenzyme. These mutant ureases maintain urease activity in the presence of fluoride ions, which are organophosphorus and organohalogen hydrolysis products that otherwise inhibit urease activity. The fluoride-resistant ureases act as effective catalytic buffers during organofluorophosphorus hydrolysis reactions. Methods for using the fluoride-resistant ureases in enzymatic decontamination are also provided. Catalytic buffering afforded by fluoride-resistant ureases facilitates the application of safe and effective enzymatic methods for decontamination of personnel, equipment and the environment.

9 Claims, 6 Drawing Sheets

FIGURE 1. DNA sequence alignment of the parental, 9-1 and 10-1 mutant urease genes

```
9-1      ATGGAACTGACCCCCCGAGAAAAAGACAAGCTGTTGCTGTTTACCGCCGCGCTGGTGGCG 60
KAU      ATGGAACTGACCCCCCGAGAAAAAGACAAGCTGTTGCTGTTTACCGCCGCGCTGGTGGCG 60
10-1     ATGGAACTGACCCCCCGAGAAAAAGACAAGCTGTTGCTGTTTACCGCCGCGCTGGTGGCG 60
         ************************************************************

9-1      GAGCGTCGCCTGGCCCGCGGCCTGAAGCTCAACTATCCGGAGTCCGTGGCCCTGATCAGC 120
KAU      GAGCGTCGCCTGGCCCGCGGCCTGAAGCTCAACTATCCGGAGTCCGTGGCCCTGATCAGC 120
10-1     GAGCGTCGCCTGGCCCGCGGCCTGAAGCTCAACTATCCGGAGTCCGTGGCCCTGATCAGC 120
         ************************************************************

9-1      GCCTTTATTATGGAAGGCGCTCGGGACGGCAAAAGCGTGGCCTCGCTGATGGAGGAAGGC 180
KAU      GCCTTTATTATGGAAGGCGCTCGGGACGGCAAAAGCGTGGCCTCGCTGATGGAGGAAGGC 180
10-1     GCCTTTATTATGGAAGGCGCTCGGGACGGCAAAAGCGTGGCCTCGCTGATGGAGGAAGGC 180
         ************************************************************

9-1      CGTCACGTCCTGACCCGCGAGCAGGTGATGGAGGGCGTCCCGGAAATGATCCCGGATATC 240
KAU      CGTCACGTCCTGACCCGCGAGCAGGTGATGGAGGGCGTCCCGGAAATGATCCCGGATATC 240
10-1     CGTCACGTCCTGACCCGCGAGCAGGTGATGGAGGGCGTCCCGGAAATGATCCCGGATATC 240
         ************************************************************

9-1      CAGGTCGAAGCCACCTTCCCGGACGGCTCGAAGCTGGTCACCGTTCACAACCCGATTATC 300
KAU      CAGGTCGAAGCCACCTTCCCGGACGGCTCGAAGCTGGTCACCGTTCACAACCCGATTATC 300
10-1     CAGGTCGAAGCCACCTTCCCGGACGGCTCGAAGCTGGTCACCGTTCACAACCCGATTATC 300
         ************************************************************

9-1      TGAGGTAGCGCCATGATCCCCGGTGAATATCACGTTAAGCCCGGTCAGATAGCCCTGAAT 360
KAU      TGAGGTAGCGCCATGATCCCCGGTGAATATCACGTTAAGCCCGGTCAGATAGCCCTGAAT 360
10-1     TGAGGTAGCGCCATGATCCCCGGTGAATATCACGTTAAGCCCGGTCAGATAGCCCTGAAT 360
         ************************************************************

9-1      ACCGGCCGGGCAACCTGTCGCGTGGTCGTTGAGAACCACGGCGATCGGCCGATTCAGGTC 420
KAU      ACCGGCCGGGCAACCTGTCGCGTGGTCGTTGAGAACCACGGCGATCGGCCGATTCAGGTC 420
10-1     ACCGGCCGGGCAACCTGTCGCGTGGTCGTTGAGAACCACGGCGATCGGCCGATTCAGGTC 420
         ************************************************************

9-1      GGTTCGCACTACCATTTCGCCGAGGTTAACCCGGCGCTGAAGTTCGACCGTCAGCAGGCC 480
KAU      GGTTCGCACTACCATTTCGCCGAGGTTAACCCGGCGCTGAAGTTCGACCGTCAGCAGGCC 480
10-1     GGTTCGCACTACCATTTCGCCGAGGTTAACCCGGCGCTGAAGTTCGACCGTCAGCAGGCC 480
         ************************************************************

9-1      GCCGGCTATCGCCTGAATATCCCGGCGGGCACGGCGGTACGCTTTGAACCCGGCCAGAAA 540
KAU      GCCGGCTATCGCCTGAATATCCCGGCGGGCACGGCGGTACGCTTTGAACCCGGCCAGAAA 540
10-1     GCCGGCTATCGCCTGAATATCCCGGCGGGCACGGCGGTACGCTTTGAACCCGGCCAGAAA 540
         ************************************************************

9-1      CGCGAGGTCGAGCTGGTGGCCTTCGCCGGTCACCGCGCCGTCTTCGGCTTCCGCGGCGAG 600
KAU      CGCGAGGTCGAGCTGGTGGCCTTCGCCGGTCACCGCGCCGTCTTCGGCTTCCGCGGCGAG 600
10-1     CGCGAGGTCGAGCTGGTGGCCTTCGCCGGTCACCGCGCCGTCTTCGGCTTCCGCGGCGAG 600
         ************************************************************

9-1      GTCATGGGCCCTCTGGAGGTAAACGATGAGTAATATTTCACGCCAGGCCTATGCCGATAT 660
KAU      GTCATGGGCCCTCTGGAGGTAAACGATGAGTAATATTTCACGCCAGGCCTATGCCGATAT 660
10-1     GTCATGGGCCCTCTGGAGGTAAACGATGAGTAATATTTCACGCCAGGCCTATGCCGATAT 660
         ************************************************************
```

```
9-1     GTTCGGCCCCACCGTCGGCGACAAGGTGCGCCTGGCAGATACCGAGCTGTGGATCGAGGT 720
KAU     GTTCGGCCCCACCGTCGGCGACAAGGTGCGCCTGGCAGATACCGAGCTGTGGATCGAGGT 720
10-1    GTTCGGCCCCACCGTCGGCGACAAGGTGCGCCTGGCAGATACCGAGCTGTGGATCGAGGT 720
        ************************************************************

9-1     GGAGGACGATTTGACCACCTACGGGGAAGAGGTCAAATTCGGCGGCGGCAAAGTGATCCG 780
KAU     GGAGGACGATTTGACCACCTACGGGGAAGAGGTCAAATTCGGCGGCGGCAAAGTGATCCG 780
10-1    GGAGGACGATTTGACCACCTACGGGGAAGAGGTCAAATTCGGCGGCGGCAAAGTGATCCG 780
        ************************************************************

9-1     CGACGGCATGGGCCAGGGACAGATGCTGGCCGCCGACTGTGTCGACCTGGTGCTCACCAA 840
KAU     CGACGGCATGGGCCAGGGACAGATGCTGGCCGCCGACTGTGTCGACCTGGTGCTCACCAA 840
10-1    CGACGGCATGGGCCAGGGACAGATGCTGGCCGCCGACTGTGTCGACCTGGTGCTCACCAA 840
        ************************************************************

9-1     CGCGTTGATCGTCGATCACTGGGGGATCGTTAAGGCCGATATCGGCGTGAAGGACGGCCG 900
KAU     CGCGTTGATCGTCGATCACTGGGGGATCGTTAAGGCCGATATCGGCGTGAAGGACGGCCG 900
10-1    CGCGTTGATCGTCGATCACTGGGGGATCGTTAAGGCCGATATCGGCGTGAAGGACGGCCG 900
        ************************************************************

9-1     GATCTTCGCCATCGGCAAAGCCGGCAACCCCGACATCCAGCCCAACGTCACCATCCCCAT 960
KAU     GATCTTCGCCATCGGCAAAGCCGGCAACCCCGACATCCAGCCCAACGTCACCATCCCCAT 960
10-1    GATCTTCGCCATCGGCAAAGCCGGCAACCCCGACATCCAGCCCAACGTCACCATCCCCAT 960
        ************************************************************

9-1     CGGCGCTGCGACGGAAGTGATCGCCGCCGAAGGAAAAATTGTCACCGCCGGCGGGATCGA 1020
KAU     CGGCGCTGCGACGGAAGTGATCGCCGCCGAAGGAAAAATTGTCACCGCCGGCGGGATCGA 1020
10-1    CGGCGCTGCGACGGAAGTGATCGCCGCCGAAGGAAAAATTGTCACCGCCGGCGGGATCGA 1020
        ************************************************************

9-1     TACCCATATTCACTGGATCTGTCCGCAGCAGGCGGAAGAGGCGCTGGTCTCTGGCGTGAC 1080
KAU     TACCCATATTCACTGGATCTGTCCGCAGCAGGCGGAAGAGGCGCTGGTCTCTGGCGTGAC 1080
10-1    TACCCATATTCACTGGATCTGTCCGCAGCAGGCGGAAGAGGCGCTGGTCTCTGGCGTGAC 1080
        ************************************************************

9-1     CACCATGGTCGGCGGCGGCACCGGCCCGGCCGCGGGCACCCATGCCACCACCTGCACCCC 1140
KAU     CACCATGGTCGGCGGCGGCACCGGCCCGGCCGCGGGCACCCATGCCACCACCTGCACCCC 1140
10-1    CACCATGGTCGGCGGCGGCACCGGCCCGGCCGCGGGCACCCATGCCACCACCTGCACCCC 1140
        ************************************************************

9-1     GGGCCCGTGGTATATCTCACGCATGCTGCAGGCGGCCGACAGCCTGCCGGTCAATATCGG 1200
KAU     GGGCCCGTGGTATATCTCACGCATGCTGCAGGCGGCCGACAGCCTGCCGGTCAATATCGG 1200
10-1    GGGCCCGTGGTATATCTCACGCATGCTGCAGGCGGCCGACAGCCTGCCGGTCAATATCGG 1200
        ************************************************************

9-1     CCTGCTGGGCAAGGGAAACGTTTCTCAGCCGGATGCCCTGCGCGAGCAGGTGGCGGCAGG 1260
KAU     CCTGCTGGGCAAGGGAAACGTTTCTCAGCCGGATGCCCTGCGCGAGCAGGTGGCGGCAGG 1260
10-1    CCTGCTGGGCAAGGGAAACGTTTCTCAGCCGGATGCCCTGCGCGAGCAGGTGGCGGCAGG 1260
        ************************************************************

9-1     CGTTATTGGCCTGAAGATCCATGAGGACTGGGGCGCCACCCCGGCGGCGATCGACTGTGC 1320
KAU     CGTTATTGGCCTGAAGATCCATGAGGACTGGGGCGCCACCCCGGCGGCGATCGACTGTGC 1320
10-1    CGTTATTGGCCTGAAGATCCATGAGGACTGGGGCGCCACCCCGGCGGCGATCGACTGTGC 1320
        ************************************************************
```

```
9-1    GTTAACCGTCGCCGATGAAATGGACATCCAGGTCGCCCTGCACAGCGACACCCTGAATGA 1380
KAU    GTTAACCGTCGCCGATGAAATGGACATCCAGGTCGCCCTGCACAGCGACACCCTGAATGA 1380
10-1   GTTAACCGTCGCCGATGAAATGGACATCCAGGTCGCCCTGCACAGCGACACCCTGAATGA 1380
       ************************************************************

9-1    ATCCGGTTTTGTGGAAGACACCCTCGCCGCCATCGGCGGGCGCACCATCCACACCTTCCA 1440
KAU    ATCCGGTTTTGTGGAAGACACCCTCGCCGCCATCGGCGGGCGCACCATCCACACCTTCCA 1440
10-1   ATCCGGTTTTGTGGAAGACACCCTCGCCGCCATCGGCGGGCGCACCATCCACACCTTCCA 1440
       ************************************************************

9-1    TACCGAAGGGGCCGGCGGCGGCCATGCGCCGGACATCATCACCGCCTGCGCCCACCCGAA 1500
KAU    TACCGAAGGGGCCGGCGGCGGCCATGCGCCGGACATCATCACCGCCTGCGCCCACCCGAA 1500
10-1   TACCGAAGGGGCCGGCGGCGGCCATGCGCCGGACATCATCACCGCCTGCGCCCACCCGAA 1500
       ************************************************************

9-1    CATTTTGCCGTCGTCCACCAACCCAACGCTGCCCTACACCCTCAACACCATCAATGAACA 1560
KAU    CATTTTGCCGTCGTCCACCAACCCAACGCTGCCCTACACCCTCAACACCATCGATGAACA 1560
10-1   CATTTTGCCGTCGTCCACCAACCCAACGCTGCCCTACACCCTCAACACCATCAATGAACA 1560
       **************************************************** *******

9-1    TCTCGATATGCTGATGGTCTGCCACCATCTGGACCCGGACATCGCCGAGGACGTGGCCTT 1620
KAU    TCTCGATATGCTGATGGTCTGCCACCATCTGGACCCGGACATCGCCGAGGACGTGGCCTT 1620
10-1   TCTCGATATACTGATGGTCTGCCACCATCTGGACCCGGACATCGCCGAGGACGTGGCCTT 1620
       ********* **************************************************

9-1    TGCCGAGTCGCGCATTCGCCGGGAAACCATCGCTGCGGAAGACGTGCTGCACGATCTCGG 1680
KAU    TGCCGAGTCGCGCATTCGCCGGGAAACCATCGCTGCGGAAGACGTGCTGCACGATCTCGG 1680
10-1   TGCCGAGTCGCGCATTCGCCGGGAAACCATCGCTGCGGAAGACGTGCTGCACGATCTCGG 1680
       ************************************************************

9-1    CGCCTTCTCGCTCACCTCCTCCGATTCGCAGGCCATGGGCCGCGTCGGGGAAGTGATTCT 1740
KAU    CGCCTTCTCGCTCACCTCCTCCGATTCGCAGGCCATGGGCCGCGTCGGGGAAGTGATTCT 1740
10-1   CGCCTTCTCGCTCACCTCCTCCGATTCGCAGGCCATGGGCCGCGTCGGGGAAGTGATTCT 1740
       ************************************************************

9-1    CCGCACCTGGCAGGTGGCGCATCGCATGAAGGTGCAGCGCGGAGCGCTGGCGGAGGAGAC 1800
KAU    CCGCACCTGGCAGGTGGCGCATCGCATGAAGGTGCAGCGCGGAGCGCTGGCGGAGGAGAC 1800
10-1   CCGCACCTGGCAGGTGGCGCATCGCATGAAGGTGCAGCGCGGAGCGCTGGCGGAGGAGAC 1800
       ************************************************************

9-1    CGGGGATAACGACAACTTCCGCGTGAAGCGCTACATCGCCAAATACACCATCAACCCGGC 1860
KAU    CGGGGATAACGACAACTTCCGCGTGAAGCGCTACATCGCCAAATACACCATCAACCCGGC 1860
10-1   CGGGGATAACGACAACTTCCGCGTGAAGCGCTACATCGCCAAATACACCATCAACCCGGC 1860
       ************************************************************

9-1    GCTGACCCACGGCATCGCACACGAAGTCGGATCCATTGAGGTGGGTAAGCTGGCTGACCT 1920
KAU    GCTGACCCACGGCATCGCACACGAAGTCGGATCCATTGAGGTGGGTAAGCTGGCTGACCT 1920
10-1   GCTGACCCACGGCATCGCACACGAAGTCGGATCCATTGAGGTGGGTAAGCTGGCTGACCT 1920
       ************************************************************

9-1    CGTGGTCTGGTCACCAGCCTTCTTCGGCGTGAAACCGGCCACCGTGATCAAAGGCGGCAT 1980
KAU    CGTGGTCTGGTCACCAGCCTTCTTCGGCGTGAAACCGGCCACCGTGATCAAAGGCGGCAT 1980
10-1   CGTGGTCTGGTCACCAGCCTTCTTCGGCGTGAAACCGGCCACCGTGATCAAAGGCGGCAT 1980
       ************************************************************

9-1    GATCGCCATCGCGCCGATGGGCGATATCAATGCCTCTATTCCGACCCCGCAGCCGGTGCA 2040
KAU    GATCGCCATCGCGCCGATGGGCGATATCAATGCCTCTATTCCGACCCCGCAGCCGGTGCA 2040
10-1   GATCGCCATCGCGCCGATGGGCGATATCAATGCCTCTATTCCGACCCCGCAGCCGGTGCA 2040
```

```
         ************************************************************

9-1      CTACCGCCCGATGTTTGGCGCGCTGGGCAGCGCCCGCCATCACTGCCGCCTCACCTTCCT 2100
KAU      CTACCGCCCGATGTTTGGCGCGCTGGGCAGCGCCCGCCATCACTGCCGCCTCACCTTCCT 2100
10-1     CTACCGCCCGATGTTTGGCGCGCTGGGCAGCGCCCGCCATCACTGCCGCCTCACCTTCCT 2100
         ************************************************************

9-1      GTCGCAGGCGGCGGCAGCCAATGGCGTTGCCGAGCGGCTGAACCTGCGCAGCGCGATCGC 2160
KAU      GTCGCAGGCGGCGGCAGCCAATGGCGTTGCCGAGCGGCTGAACCTGCGCAGCGCGATCGC 2160
10-1     GTCGCAGGCGGCGGCAGCCAATGGCGTTGCCGAGCGGCTGAACCTGCGCAGCGCGATCGC 2160
         ************************************************************

9-1      CGTGGTGAAAGGCTGCCGTACGGTGCAGAAAGCCGACATGGTGCACAACAGTCTGCAGCC 2220
KAU      CGTGGTGAAAGGCTGCCGTACGGTGCAGAAAGCCGACATGGTGCACAACAGTCTGCAGCC 2220
10-1     CGTGGTGAAAGGCTGCCGTACGGTGCAGAAAGCCGACATGGTGCACAACAGTCTGCAGCC 2220
         ************************************************************

9-1      TAACATCACCGTCGACGCCCAGACCTATGAGGTGCGGGTGGATGGCGAACTTATCACCAG 2280
KAU      TAACATCACCGTCGACGCCCAGACCTATGAGGTGCGGGTGGATGGCGAACTTATCACCAG 2280
10-1     TAACATCACCGTCGACGCCCAGACCTATGAGGTGCGGGTGGATGGCGAACTTATCACCAG 2280
         ************************************************************

9-1      CGAGCCGGCAGACGTTCTGCCGATGGCGCAACGATATTTTCTGTTTTAA 2329
KAU      CGAGCCGGCAGACGTTCTGCCGATGGCGCAACGATATTTTCTGTTTTAA 2329
10-1     CGAGCCGGCAGACGTTCTGCCGATGGCGCAACGATATTTTCTGTTTTAA 2329
         *************************************************
```

Figure 2. Comparison of alpha subunit amino acid sequences encoded by the ureC genes of the parental, 9-1 and 10-1 mutant ureases

```
9-1     MSNISRQAYADMFGPTVGDKVRLADTELWIEVEDDLTTYGEEVKFGGGKVIRDGMGQGQM 60
10-1    MSNISRQAYADMFGPTVGDKVRLADTELWIEVEDDLTTYGEEVKFGGGKVIRDGMGQGQM 60
KAU     MSNISRQAYADMFGPTVGDKVRLADTELWIEVEDDLTTYGEEVKFGGGKVIRDGMGQGQM 60
        ************************************************************

9-1     LAADCVDLVLTNALIVDHWGIVKADIGVKDGRIFAIGKAGNPDIQPNVTIPIGAATEVIA 120
10-1    LAADCVDLVLTNALIVDHWGIVKADIGVKDGRIFAIGKAGNPDIQPNVTIPIGAATEVIA 120
KAU     LAADCVDLVLTNALIVDHWGIVKADIGVKDGRIFAIGKAGNPDIQPNVTIPIGAATEVIA 120
        ************************************************************

9-1     AEGKIVTAGGIDTHIHWICPQQAEEALVSGVTTMVGGGTGPAAGTHATTCTPGPWYISRM 180
10-1    AEGKIVTAGGIDTHIHWICPQQAEEALVSGVTTMVGGGTGPAAGTHATTCTPGPWYISRM 180
KAU     AEGKIVTAGGIDTHIHWICPQQAEEALVSGVTTMVGGGTGPAAGTHATTCTPGPWYISRM 180
        ************************************************************

9-1     LQAADSLPVNIGLLGKGNVSQPDALREQVAAGVIGLKIHEDWGATPAAIDCALTVADEMD 240
10-1    LQAADSLPVNIGLLGKGNVSQPDALREQVAAGVIGLKIHEDWGATPAAIDCALTVADEMD 240
KAU     LQAADSLPVNIGLLGKGNVSQPDALREQVAAGVIGLKIHEDWGATPAAIDCALTVADEMD 240
        ************************************************************

9-1     IQVALHSDTLNESGFVEDTLAAIGGRTIHTFHTEGAGGGHAPDIITACAHPNILPSSTNP 300
10-1    IQVALHSDTLNESGFVEDTLAAIGGRTIHTFHTEGAGGGHAPDIITACAHPNILPSSTNP 300
KAU     IQVALHSDTLNESGFVEDTLAAIGGRTIHTFHTEGAGGGHAPDIITACAHPNILPSSTNP 300
        ************************************************************

9-1     TLPYTLNTINEHLDMLMVCHHLDPDIAEDVAFAESRIRRETIAAEDVLHDLGAFSLTSSD 360
10-1    TLPYTLNTINEHLDILMVCHHLDPDIAEDVAFAESRIRRETIAAEDVLHDLGAFSLTSSD 360
KAU     TLPYTLNTIDEHLDMLMVCHHLDPDIAEDVAFAESRIRRETIAAEDVLHDLGAFSLTSSD 360
        ********* **** *********************************************

9-1     SQAMGRVGEVILRTWQVAHRMKVQRGALAEETGDNDNFRVKRYIAKYTINPALTHGIAHE 420
10-1    SQAMGRVGEVILRTWQVAHRMKVQRGALAEETGDNDNFRVKRYIAKYTINPALTHGIAHE 420
KAU     SQAMGRVGEVILRTWQVAHRMKVQRGALAEETGDNDNFRVKRYIAKYTINPALTHGIAHE 420
        ************************************************************

9-1     VGSIEVGKLADLVVWSPAFFGVKPATVIKGGMIAIAPMGDINASIPTPQPVHYRPMFGAL 480
10-1    VGSIEVGKLADLVVWSPAFFGVKPATVIKGGMIAIAPMGDINASIPTPQPVHYRPMFGAL 480
KAU     VGSIEVGKLADLVVWSPAFFGVKPATVIKGGMIAIAPMGDINASIPTPQPVHYRPMFGAL 480
        ************************************************************

9-1     GSARHHCRLTFLSQAAAANGVAERLNLRSAIAVVKGCRTVQKADMVHNSLQPNITVDAQT 540
10-1    GSARHHCRLTFLSQAAAANGVAERLNLRSAIAVVKGCRTVQKADMVHNSLQPNITVDAQT 540
KAU     GSARHHCRLTFLSQAAAANGVAERLNLRSAIAVVKGCRTVQKADMVHNSLQPNITVDAQT 540
        ************************************************************

9-1     YEVRVDGELITSEPADVLPMAQRYFLF 567
10-1    YEVRVDGELITSEPADVLPMAQRYFLF 567
KAU     YEVRVDGELITSEPADVLPMAQRYFLF 567
        ***************************
```

CATALYTIC BUFFERING SYSTEMS

GOVERNMENTAL INTEREST

The invention described herein may be manufactured, used and licensed by or for the U.S. Government.

TECHNICAL FIELD

This invention relates to materials and methods involved in catalytic buffering, particularly for enzymatic decontamination.

BACKGROUND

Biohazardous agents encompass a wide range of chemical compounds used in agricultural, military and industrial applications. Some organophosphorus compounds used in agricultural and military applications are highly toxic and hazardous to both human health and the environment. Organophosphorus compounds comprise the active ingredient in pesticides such as parathion and in G-type nerve agents such as Sarin, Soman and VX, developed for chemical warfare. The nerve agents, which can be absorbed through both skin contact and inhalation, exert their lethal effects by inhibition of acetylcholinesterase, an enzyme critical for neurotransmission. Halogenated compounds (organohalogens) which are commonly found in solvents and pesticides present both acute and long term hazards to the environment and human health. In light of the serious health risks posed by both organophosphorus compounds and organohalogens, it is essential to be able to detoxify these molecules and to decontaminate surfaces and substances contaminated with these agents.

Chemical based decontamination solutions such as DS2 have toxic and corrosive properties. Enzymatic techniques, using hydrolytic enzymes, are water-based and distinguished by low toxicities, making them relatively non-hazardous to personnel, equipment and the environment Control of pH is essential for enzyme-based chemical warfare agent decontamination and other hydrolytic systems. Conventional chemical buffers have limited capacity to maintain the pH near the optimum for the organophosphorus or organohalogen hydrolyzing enzymes. Catalytic buffering, in contrast, relies upon enzymes to produce ions from a substrate in order to regulate the pH of a solution. Effective catalytic buffering of enzymatic decontamination reactions requires that the catalytic buffering enzyme be active under the reaction conditions required for the organophosphorus hydrolyzing enzymes.

SUMMARY

This document provides material and methods for catalytic buffering of enzymatic decontamination reactions. Enzymatic decontamination of organophosphorus and halogenated compounds generates highly acidic reaction products that precipitously reduce the pH of the surrounding medium, thus impairing the activity of the decontaminating enzymes. Catalytic buffering, that is, the use of an enzyme to produce ions from a substrate in order to regulate the pH of a solution, can provide an effective means of pH control, particularly in situations such as organophosphorus hydrolysis where the buffering capacity of conventional chemical buffers is rapidly exceeded. The materials and methods described here provide fluoride-resistant urease enzymes that maintain urease activity in the presence of fluoride ions, which are products of hydrolysis of organofluorophosphorus and other halogenated compounds that otherwise inhibit urease activity. Catalysis of urea by these fluoride resistant ureases produces ammonium ions that neutralize the acidic hydrolytic reaction products. The catalytic buffering afforded by the fluoride-resistant ureases facilitates the application of safe and effective enzymatic methods for decontamination of personnel, equipment and the surrounding environment.

In one aspect, this document provides isolated nucleic acids comprising a sequence encoding mutations in the alpha subunit polypeptide of the urease holoenzyme wherein the sequence comprises a fluoride resistance mutation when the mutant alpha subunit polypeptide is incorporated into the urease holoenzyme. For example, a mutation in the nucleic acid of the invention can result in a mutation at the codon encoding amino acid 310 in the reference sequence set forth in SEQ ID NO:1.

In another example, a mutation in the nucleic acid of the invention can result in a mutation at the codon encoding amino acid 310 and amino acid 315 in the reference sequence set forth in SEQ ID NO:1.

In another aspect, this document provides a substantially pure urease alpha subunit polypeptide, wherein the polypeptide comprises a fluoride resistance mutation when the polypeptide is incorporated into the urease holoenzyme.

In another aspect, this document provides a substantially pure recombinant urease enzyme wherein the recombinant urease enzyme comprises a fluoride resistance mutation in the alpha subunit.

In another example, a recombinant DNA construct for expressing a mutant urease in prokaryotic cells, the construct comprising a prokaryotic promoter operably linked to a DNA fragment comprising a nucleotide sequence encoding a urease alpha subunit polypeptide where the sequence comprises a fluoride resistance mutation, is provided.

In another aspect, methods of using fluoride resistant ureases to decontaminate surfaces or substances contaminated with organophosphorus or halogenated compounds are provided. In another example, methods of using fluoride resistant ureases to detoxify stocks of organophosphorus or halogenated compounds are provided. This document also provides a composition comprising an organophosphorus or organohalogen hydrolyzing enzyme or enzymes, an ammonium ion, a mutant urease enzyme comprising a fluoride resistance mutation in the alpha subunit, and urea for hydrolytic enzymatic decontamination reactions.

In another aspect, this document provides a kit useful for enzymatic decontamination of organophosphorus or organohalogen hydrolysis reactions. The kit can include packaging material, instructional material and measured amounts of an organophosphorus or organohalogen hydrolyzing enzyme or enzymes, an ammonium ion, a mutant urease enzyme comprising a fluoride resistance mutation in the alpha subunit, and urea.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF SEQUENCES

SEQ ID NO:1 is the amino acid sequence of the *Klebsiella aerogenes* urease alpha subunit polypeptide encoded by SEQ ID NO:2.

SEQ ID NO:2 is the nucleotide sequence of *Klebsiella aerogenes* urease ureC gene.

SEQ ID NO:3 is the nucleotide sequence of *Klebsiella aerogenes* urease mutant 9-1 ureC gene.

SEQ ID NO:4 is the nucleotide sequence of *Klebsiella aerogenes* urease mutant 10-1 ureC gene.

SEQ ID NO:5 is the amino acid sequence of the *Klebsiella aerogenes* urease mutant 9-1 alpha subunit polypeptide encoded by SEQ ID NO:3.

SEQ ID NO:6 is the amino acid sequence of the *Klebsiella aerogenes* urease mutant 10-1 alpha subunit polypeptide encoded by SEQ ID NO:4.

SEQ ID NO:7 is the nucleotide sequence of *Klebsiella aerogenes* urease ureABC genes.

SEQ ID NO:8 is the nucleotide sequence of *Klebsiella aerogenes* urease mutant 9-1 ureABC genes.

SEQ ID NO:9 is the nucleotide sequence of *Klebsiella aerogenes* urease mutant 10-1 ureABC genes.

DESCRIPTION OF DRAWINGS

FIG. 1 is a DNA sequence alignment of the parental (KAU) (SEQ ID NO:7), 9-1 (SEQ ID NO:8) and 10-1 (SEQ ID NO:9) mutant urease genes. Only the 5'-3' single strands are shown. Gene regions for the urease subunits are: ureA is encoded by nucleotides 1-303; ureB is encoded by nucleotides 313-633; ureC is encoded by nucleotides 626-2329. One letter representations of the four bases are shown. Mutations are bold and underlined. Homologous three-way nucleotide sequence matches are indicated by the symbol * below the sequence groups.

FIG. 2 is a comparison of the alpha subunit amino acid sequences encoded by the ureC genes of the parental (KAU) (SEQ ID NO:1), 9-1 (SEQ ID NO:5) and 10-1 (SEQ ID NO:6) mutant ureases. One letter amino acid codes are shown. Mutations are bold and underlined. Homologous three-way amino acid sequence matches are indicated by the symbol * below the sequence groups.

Like reference symbols in the various drawings indicate like elements.

DETAILED DESCRIPTION

Figure 3:
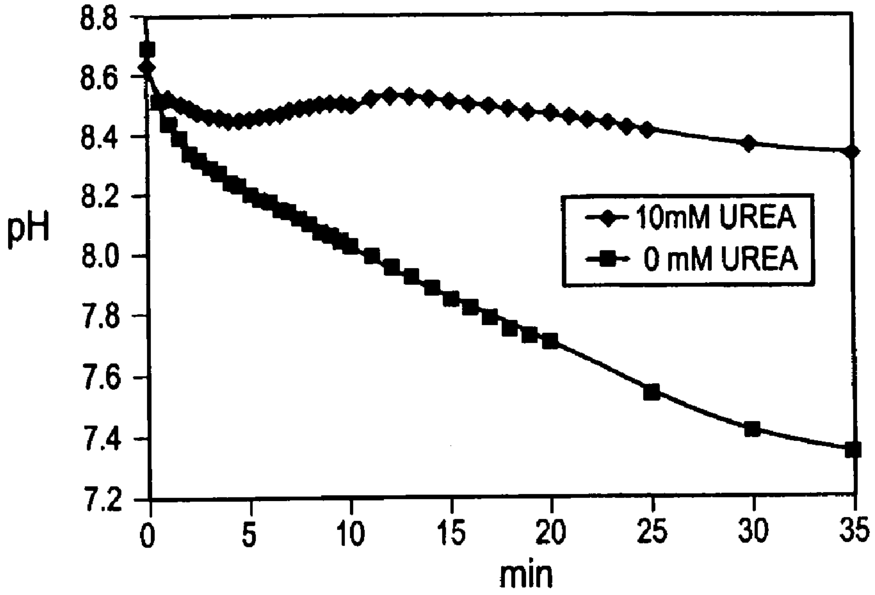
FIG. 3 shows catalytic buffering of organophosphorus acid anhydrolase (OPAA) hydrolysis of DFP with 9-1 urease. Reactions contained 16 ug/mL OPAA, 1.5 units/mL of 9-1 urease, 3 mM DFP, and 5 mM ammonium carbonate, in the presence (diamond symbols) or absence (square symbols) of 10 mM urea. Reaction temperature was 25° C.

This document provides materials and methods related to catalytic buffering of enzymatic decontamination reactions.

The term "catalytic buffering" refers to the use of a catalyst, e.g. an enzyme, to produce ions from a substrate in order to regulate the pH of a solution. Enzymatic breakdown of organofluorophosphorus compounds by organophosphorus hydrolyzing enzymes yields acidic O-alkylphosphonate compounds and fluoride ions as shown in the example below.

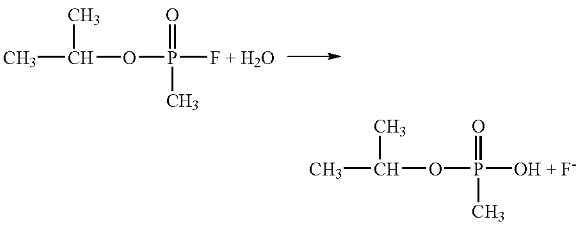

Accumulation of the O-alkylphosphonates results in a rapid fall in the pH of the surrounding medium which in turn results in the rapid decrease in the efficiency of enzymatic hydrolysis since the pH optimum for organophosphorus hydrolyzing enzymes is above 8.0. Similarly, the enzymatic hydrolysis of halogenated organic compounds generates acids that must be neutralized in order to maintain enzymatic activity.

The enzyme urease, by hydrolysis of its substrate, urea, generates ammonium ions according to the reaction below, that can neutralize acid production and effectively stabilize pH.

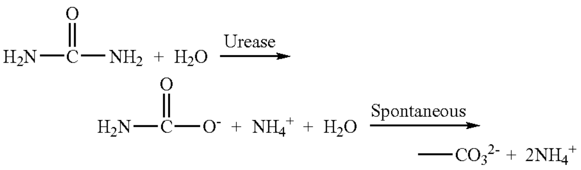

The materials and methods described here provide fluoride-resistant urease enzymes that maintain urease activity in the presence of fluoride ions, which are products of organophosphorus or organohalogen hydrolysis that otherwise inhibit urease activity. The mutant urease enzymes described in this document efficiently catalyze the hydrolysis of urea in the presence of fluoride ions, thus providing an effective catalytic buffering system for enzymatic decontamination of organophosphorus or organohalogen hydrolysis reactions.

This document provides materials and methods for catalytic buffering of enzymatic decontamination reactions using fluoride resistant ureases. Thus, in one aspect, this document features mutant urease enzymes that are active in the presence of fluoride ions. In another aspect, this document features methods and materials for using fluoride resistant ureases as catalytic buffers in enzymatic decontamination systems.

I. DEFINITIONS

Nucleic acids. This document provides isolated nucleic acid molecules that encode a *Klebsiella aerogenes* urease alpha subunit polypeptide (e.g., SEQ ID NO:1). The term "parental" or "wild-type" as used herein with respect to the urease alpha subunit polypeptide refers to the nucleic acid sequence referenced in SEQ ID NO:1 (i.e. the “parental” or “wild-type” nucleic acid sequence provided in SEQ ID NO:2). A nucleic acid molecule encoding a urease polypeptide can include one or more mutations such as those provided in SEQ ID NOs: 3 and 4. As used herein, the term “isolated” as used in reference to a nucleic acid refers to nucleic acid that is separated from other nucleic acid that is present in a genome, including nucleic acids that normally flank one or both sides of the nucleic acid in a genome (e.g., nucleic acids that encode non-urease polypeptides). The term “isolated” as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, cDNA, or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

The nucleic acids provided herein can be at least about 8 nucleotides in length. For example, a nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, 1000, 2000, 3000, or 4000 nucleotides in length). In some embodiments, a nucleic acid can be in a sense or antisense orientation, can be complementary to a reference sequence encoding a urease alpha subunit polypeptide (e.g., SEQ ID NO:1), and can be DNA, RNA, or nucleic acid analogs. Nucleic acid analogs can be modified at the base moiety, sugar moiety, or phosphate backbone to improve, for example, stability, hybridization, or solubility of the nucleic acid.

Types of mutations that a nucleic acid encoding a urease polypeptide can carry include, without limitation, insertions, deletions, transitions, transversions and inversions. A nucleic acid encoding a urease polypeptide can include more than one mutation and more than one type of mutation. Such mutations, if present within the coding sequence, can result in insertions or deletions of one or more amino acids of a urease polypeptide, conservative or non-conservative amino acid substitutions within a urease polypeptide, or premature termination of a urease polypeptide. Insertion or deletion of amino acids can, for example, disrupt the conformation of essential α-helical or β-pleated sheet regions, and can also disrupt binding or catalytic sites important for enzymatic activity. Non-conservative amino acid substitutions can result in a substantial change in the bulk of the residue side chain, and ultimately can make a substantial change in the charge, hydrophobicity, or structure of a polypeptide. Premature termination also can cause disruptions in secondary and tertiary polypeptide structure. In addition, non-coding sequence mutations (e.g., mutations in a promoter, regulatory element, or untranslated region) can alter the expression pattern properties (e.g., temporal, spatial, or developmental) of a urease polypeptide, by, for example, changing the binding characteristics of a cis-acting transcription factor.

In some embodiments, a nucleic acid molecule provided herein can have at least 95% (e.g., 96%, 97%, 98%, 99%, 99.5%, 99.6%, 99.7%, 99.8%, 99.9%, or 100%) sequence identity with a region of a reference sequence (e.g., SEQ ID NO:1 (GenBank Accession No. M36068)), provided that the region includes one or more mutations. Such mutations are those, for example, described herein. The region is at least ten nucleotides in length (e.g., 10, 15, 20, 50, 60, 70, 75, 100, 150, 200, 250, 300, 350, 400, 450, 500, or more than 500 nucleotides in length).

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

As used herein, the term “percent sequence identity” refers to the degree of identity between any given query sequence and a subject sequence. A percent identity for any query nucleic acid or amino acid sequence, e.g., a transcription factor, relative to another subject nucleic acid or amino acid sequence can be determined as follows.

A query nucleic acid or amino acid sequence is aligned to one or more subject nucleic acid or amino acid sequences using the computer program ClustalW (version 1.82) which allows alignments of nucleic acid or protein sequences to be carried out across their entire length (global alignment).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For alignment of multiple nucleic acid sequences, the following parameters can be used: gap opening penalty: 15.0; gap extension penalty: 6.66; and weight transitions: yes. For fast pairwise alignment of protein sequences, the following parameters were used: word size: 1; window size: 5; scoring method: percentage; number of top diagonals: 5; gap penalty: 3. The output is a sequence alignment that reflects the relationship between sequences. ClustalW can be run, for example, at the Baylor College of Medicine Search Launcher site searchlauncher.bcm.tmc.edu/multi-align/multi-align.html and at the European Bioinformatics Institute site ebi.ac.uk/clustalw. To determine a percent identity between a query sequence and a subject sequence, the number of matching bases or amino acids in the alignment is divided by the total number of matched and mis-matched bases or amino acids excluding gaps, followed by multiplying the result by 100. The output is the percent identity of the subject sequence with respect to the query sequence.

Urease activity is detectable in both microorganisms and plants (Mobley et al., 1995) and the urease gene clusters are evolutionarily conserved. For example, DNA encoding the alpha subunit polypeptide may be obtained from *Escherichia coli, Pseudomonas putida, Proteus mirabilis, Proteus vulgaris*, and *Bacillus pasteurii*. Bacterial strains can be obtained from any source, for example, The American Type Culture Collection. The isolated nucleic acids provided herein can be produced by standard techniques, including, without limitation, common molecular cloning and chemical nucleic acid synthesis techniques. For example, polymerase chain reaction (PCR) techniques can be used to obtain an isolated nucleic acid containing a mutation. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in PCR Primer: A Laboratory Manual, ed. by Dieffenbach and Dveksler, Cold Spring Harbor Laboratory Press, 1995. When using RNA as a source of template, reverse transcriptase can be used to synthesize cDNA strands. Ligase chain reaction, strand displacement amplification, self-sustained sequence replication, or nucleic acid sequence-based amplification also can be used to obtain isolated nucleic acids. See, for example, Lewis, Genetic Engineering News, 12(9):1 (1992); Guatelli et al., Proc. Natl. Acad. Sci. USA, 87:1874-1878 (1990); and Weiss, Science, 254:1292 (1991).

The isolated nucleic acids provided herein also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. A DNA polymerase can be used to extend the oligonucleotides, resulting in a single, double-stranded nucleic acid molecule per oligonucleotide pair, which then can be ligated into a vector.

Polypeptides. In one aspect, this application provides mutant urease alpha subunit polypeptides. A urease alpha subunit polypeptide can have mutant amino acid sequences shown in SEQ ID NOs: 5 and 6. Urease polypeptides of the invention can have at least 95% sequence identify to the reference (wild-type) urease polypeptide sequence shown, for example, in SEQ ID NO:1 (e.g., GenBank Accession No. M36068). Urease alpha subunit polypeptides are polypeptides that assemble together with the beta and gamma subunits to form the multimeric apoenzyme containing three copies each of an alpha, beta and gamma subunits ($\alpha_3\beta_3\gamma_3$). The urease polypeptides may be present in a crude cellular extract, a cell lysate or partially or substantially pure.

The term "substantially pure" with respect to a naturally-occurring urease polypeptide refers to a polypeptide that has been separated from cellular components by which it is naturally accompanied, such that it is at least 60% (e.g., 70%, 80%, 90%, 95%, or 99%), by weight, free from polypeptides and naturally-occurring organic molecules with which it is naturally associated. In general, a substantially pure polypeptide will yield a single major band on a non-reducing polyacrylamide gel.

A substantially pure polypeptide provided herein can be obtained by, for example, extraction from a natural source (e.g., a microorganism or plant), chemical synthesis, or by recombinant production in a host cell. To produce a recombinant urease polypeptide, a nucleic acid encoding urease can be ligated into an expression vector and used to transform a prokaryotic (e.g., bacteria) or eukaryotic (e.g., insect, yeast, or mammal) host cell. In general, nucleic acid constructs can include a regulatory sequence operably linked to a nucleic acid encoding a urease polypeptide. Regulatory sequences (e.g., promoters, enhancers, polyadenylation signals, or terminators) do not typically encode a gene product, but instead affect the expression of a nucleic acid sequence.

A construct can include a tag sequence designed to facilitate subsequent manipulations of the expressed nucleic acid sequence (e.g., purification, localization, etc.). Tag sequences, such as green fluorescent protein (GFP), glutathione S-transferase (GST), c-myc, hemagglutinin, or Flag™ tag (Kodak) sequences are typically expressed as a fusion with the polypeptide encoded by the nucleic acid sequence. Such tags can be inserted in a nucleic acid sequence such that they are expressed anywhere along an encoded polypeptide including, for example, at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include, without limitation, pBAD (Invitrogen, Carlsbad, Calif.), the pTYB family of vectors (New England Biolabs), and pGEMEX vectors (Promega); representative mammalian expression vectors include, without limitation, pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include, without limitation, pBacPAK8 or pBacPAK9 (Clontech), and p2Bac (Invitrogen); and representative yeast expression vectors include, without limitation, MATCHMAKER (Clontech) and pPICZ A, B, and C (Invitrogen).

In bacterial systems, *Escherichia coli* can be used to express urease polypeptides. For example, the *E. coli* strain DH10B (Invitrogen) can be transformed with the gram negative broad host range vector, pCM66 containing a nucleic acid sequence encoding a urease polypeptide. In another example, BL-21 cells can be transformed with a pGEX vector containing a nucleic acid sequence encoding a urease polypeptide. The transformed bacteria can be grown exponentially and then stimulated with isopropylthiogalactopyranoside (IPTG) prior to harvesting. In general, the urease-GST fusion polypeptides produced from a pGEX expression vector can be purified from lysed cells by adsorption to glutathione-agarose beads followed by elution in the presence of free glutathione. The pGEX vectors can be designed to include thrombin or factor Xa protease cleavage sites so that the expressed urease polypeptide can be released from the GST moiety.

Urease polypeptides and mutants thereof can be purified by known chromatographic methods including ion exchange and gel filtration chromatography. See, for example, Caine et al., Protein Expr. Purif. (1996) 8(2):159-166. Urease polypeptides also can be "engineered" to contain a tag sequence describe herein that allows the polypeptide to be purified (e.g., captured onto an affinity matrix). In addition, immunoaffinity chromatography can be used to purify urease polypeptides or mutants thereof. Protein concentration can be determined by any standard method. The urease holoenzyme is a multisubunit metalloenzyme that requires bound nickel for activity (Mobley et al., Microbiological Reviews 59: 451-480, 1995). Nickel is inserted into the apoprotein by the action of the accessory genes ureD, ureF and ureG, a process that is facilitated by ureE, a putative metallochaperone that delivers nickel ion. Enzymatically active holoenzyme can be obtained by standard methods including transformation of a bacterial host with a plasmid encoding the urease operon (Genbank accession numbers M36068 and L07039); cotransformation of a bacterial host with a plasmid encoding the ureABC structural genes and a second plasmid encoding the accessory genes ureDEFG (GenBank accession numbers M36068 and L07039); or by transformation of a bacterial host with a plasmid encoding the structural genes, ureA, ureB and ureC and relying upon the accessory genes present in the host chromosome to provide the accessory gene products for assembling active holoenzyme.

II. MUTANT UREASES

Mutant urease enzymes can be generated by any standard method of mutagenesis. In vivo approaches may involve exposure of bacterial cells to mutagenizing chemicals or agents, such as ultraviolet light. Molecular biology-based methods of mutagenesis can include random or site-directed techniques. Random mutagenesis methods can include error-prone PCR, rolling circle amplification and the use of bacterial mutator strains. In one embodiment, random mutations in the ureABC urease structural genes can be obtained by propagating a plasmid containing the structural genes in bacterial strains that are engineered to have high spontaneous mutation rates, such as *E. coli* XL1-Red (Stratagene). Repeated rounds of mutagenesis and selection can be used to further generate mutant urease genes. Mutant urease genes can also be obtained through site-directed mutagenesis using, for example, either PCR or non-PCR based techniques.

Identification of bacterial strains carrying mutant urease enzymes can be carried out by assaying urease activity in the presence of fluoride ions. Enzymatic activity can be assayed on *E. coli* transformants in situ, in colonies transferred to filters, or in extracts prepared from single colonies grown in liquid culture. In one embodiment, *E. coli* cells co-transformed with a plasmid encoding any mutant urease structural genes and a plasmid encoding the urease accessory genes can be grown on agar plates and the colonies transferred to filters. Following colony lysis with $CHCl_3$, the filters can be placed on pads soaked with a buffered colorimetric assay solution containing 0.1M NaF and urea. Colonies expressing active fluoride resistant ureases will turn from yellow to red; colonies with wild-type urease will show no color change. Regrowth of colonies on the agar plates can allow recovery of bacteria expressing ureases that are active in the presence of fluoride ions. The location and type of mutations in the urease structural genes can be determined using any standard method of nucleic acid sequencing; the amino acid sequence can be deduced from the nucleotide sequence.

Urease activity can be assayed on partially or highly purified urease enzymes by any standard enzymological method. For example, urease activity can be monitored by measuring the ammonia released during the reaction, either colorimetrically with phenol-hypochlorite or Nessler's reagent (Sigma Chemical Company); spectrophotometrically in a coupled NADH-dependent glutamate dehydrogenase assay; or by ammonium-ion selective electrodes. Urease activity can also be assayed using a radiolabeled substrate such as [$^{14}$C]urea and measuring the accumulation of $^{14}CO_2$ by scintillation counting. Since urea hydrolysis results in an increase in pH, pH-dependent assays, for example, those based on pH sensitive dyes, may also be used.

Urease activity can be assayed in the presence of any concentration (e.g. 0, 1, 2, 5, 10, 15, 20, 40, 50, 100, 200 mM) of fluoride ions. As used herein to describe mutant ureases, the term "fluoride resistance" means a mutation which, when present, results in significant activity in a concentration of fluoride ions that would inhibit a wild-type enzyme in the presence of the same concentration of fluoride ions. For example, fluoride inhibition constant values (Ki) reported for urease enzymes have ranged from 0.2 mM for urease from *Klebsiella aerogenes* to 1 mM for Jack Bean urease at neutral pH (Todd, M. J. and Hausinger, Biochemistry, 39: 5389-5396, 2000). The activity of the mutant ureases can be increased in the presence of fluoride ions relative to the activity of the parental or wild-type urease by any amount. For example, the increase can be 1, 2, 5, 10, 15, 20, 25, 30, 35, 40, 50, 75, 100, 200-fold or more higher than the activity in the parental urease on a weight basis. In some embodiments, the activity of the mutant ureases can be increased or decreased in the absence of fluoride ions relative to the parental urease. For example, in the absence of fluoride ions, the urease activity of the mutant enzyme can be 1, 2, 5, 10, 20, 50, or 100-fold or greater than that of the parental urease. In another example, in the absence of fluoride ions, the urease activity of the mutant enzyme can be 1, 2, 5, or 10-fold less than that of the parental urease.

The urease activity of different mutant enzymes relative to that of the parental enzyme can vary according to fluoride ion concentration. For example, a particular mutation may confer higher specific activity at lower fluoride ion concentrations (e.g. below 2, 5, 10, 20, and 40 mM) while another mutation may confer higher specific activity at higher fluoride ion concentrations (e.g. above 5, 10, 20, 40, 50 and 100 mM).

In some embodiments, different alpha subunit mutations may be expressed in the same host. For example, since the mature enzyme contains three alpha subunits, recombinant ureases having a mixture of different alpha subunits can be generated.

III. CATALYTIC BUFFERING

This document features methods and materials for using fluoride resistant ureases as catalytic buffers in enzymatic decontamination systems.

The mutant urease enzymes described in this document can be used, with the addition of the urea substrate, to buffer organophosphorus or organohalogen hydrolysis reactions that lead to a pH decrease by any amount (e.g. 0.1, 0.2, 0.4, 0.6, 0.8, 1.0, 1.2, 1.4, 1.6, 1.8, 2.0, 2.5, 3.0, 3.5, 4.0, 4.5, 5.0, 5.5, 6.0, 6.5, 7.0, 7.5 or more pH units) below the initial pH of the reaction. For example, the mutant urease enzymes described in this document can be used, with the addition of the urea substrate, to buffer organophosphorus or organohalogen hydrolysis reactions that lead to a pH decrease by any amount (e.g. 0.1, 0.2, 0.4, 0.6, 0.8, 1.0, 1.2, 1.4, 1.6, 1.8, 2.0, 2.5, 3.0, 3.5, 4.0, 4.5, 5.0, 5.5, 6.0, 6.5, 7.0, 7.5 or more pH units) when compared with the pH observed in the presence of the urease and urea.

Ureases having different mutations that confer activity on the presence of fluoride ions can be used alone or as a combination of different mutant enzymes. For example, ureases that are more active at fluoride ion concentrations below 20 mM may buffer most efficiently during the initial stages of enzymatic decontamination; while those ureases that are most active at fluoride concentrations above 20 mM may buffer most effectively during the later stages of enzymatic decontamination, after significant accumulation of fluoride ions has occurred.

The mutant urease enzymes may be added to reactions that include any organophosphorus or organohalogen hydrolyzing enzymes. For example, the mutant ureases may be added to reactions that include, but are not limited to, organophosphorus hydrolase, organophosphorus acid anhydrolase, organophosphorus acid anhydrolase-2, prolidase (EC 3.4.13.9), Loligo vulgaris dialkylfluorophosphatase and haloalkane dehydrogenases (E.C. 3.8.1.5). Organophosphorus or organohalogen hydrolyzing enzymes may be obtained from naturally occurring sources (e.g. microorganisms or marine organisms), chemical synthesis, or recombinant production in a host cell.

The mutant urease enzymes may be used in reactions that include any chemical buffering system. For example, the mutant ureases may be added to reactions that include ammonium acetate, ammonium carbonate, ammonium formate, bis-tris-propane, bicine, CAPS, CHES, citrate-phosphate, HEPBS, HEPES, TAPS, AMPD, and Tris-HCl. The mutant urease enzymes described in this document may be used for catalytic buffering of hydrolysis reactions of any suitable substrate for organophosphorus hydrolyzing enzymes. For example, substrates can include G-type nerve agents developed for chemical warfare such as Sarin (GB; o-isopropyl methylphosphonofluoridate); Soman (GD; o-pinacolyl methylphosphonofluoridate); GF (o-cyclohexyl methylphosphonofluoridate); VX (S-2(diisopropyl) methyl o-ethylphosphonothioate); and tabun (GA; N,N-dimethylethyl phosphoroamidocyanidate) and the nerve agent analogue, DFP (diisopropyl fluorophosphate.).

In another embodiment, mutant ureases having elevated activity relative to the parental enzymes may also be used as catalytic buffers in any reaction in which the activity of the organophosphorus or organohalogen hydrolyzing enzymes results in a decrease in pH. For example, these reactions can include enzymatic hydrolysis of organophosphorus pesticides such as parathion and paraoxon, organochlorine-based pesticides and chlorinated solvents.

IV. ENZYMATIC DECONTAMINATION

This document features methods and materials for using fluoride resistant ureases as catalytic buffers in enzymatic decontamination systems for the decontamination of surfaces or substances that are contaminated with organophosphorus or organohalogen compounds. For example, the surfaces or substances may be any surface or substance contaminated with organophosphorus or organohalogen compounds including but not limited to buildings and their contents, vehicles, military equipment, transportation systems, water supplies and infrastructure, community infrastructure, people, animals and the natural environment including soil, plants and bodies of water.

Contaminated surfaces or substances may be formed or otherwise arise as a result of any number of processes, methods or triggering events, including but not limited to, chemical warfare attacks, military operations, chemical manufacturing, scientific research, agricultural application of pesticides, toxic waste storage, and accidental spills occurring during the use of any organophosphorus or organohalogen compound.

The materials and methods supplied herein may be applied to contaminated surfaces or substances in any formulation suitable for decontamination. The formulation may include, but is not limited to, biodegradable water soluble materials such as foams, wetting agents or degreasers, for example, AFC-380®, BioSolve®, BV 406LF®, Cold Fire Retardant®, Cold Fire®, Eco-Foam™ (AR/AFFF, MS3, TF), F-500, Fire Choke, Hawk (A-B, Class A, Class B, ALLFIRE), National Foam (Aer-O-Water®, Universal® Gold, Universal® Plus), Odor Seal®, PhosChek®, and Tide® Free laundry detergent. The material may also be prepared in any formulation suitable for use in humans or animals. The enzymatic decontamination reagents supplied herein also may be granulated or lyophilized, using any standard method of granulation or lyophilization, for long term storage and then reconstituted at their point of use. A granulated/lyophilized composition may include reagents that aid in stability of enzymes during the granularization/lyophilization and reconstitution process. Such reagents may include, but are not limited to, sorbitol, sucrose, trehalose, glycerol, and $MnCl_2$. In another embodiment, the materials and methods provided in this document may be used to detoxify stocks of organophosphorus compounds. Stocks of organophosphorus compounds may include, but are not limited to chemical warfare agents, pesticides, chlorinated solvents, and toxic wastes. Other compounds that could be detoxified include, but are not limited to, chlorinated solvents and toxic wastes.

The reagents used for enzymatic decontamination can be combined as an article of manufacture, for example, as a kit, In one embodiment, the article can comprise an organophosphorus or organohalogen hydrolyzing enzyme, a mutant urease enzyme, urea and chemical buffers such as ammonium carbonate. Such kits may also include reagents that promote the stability of the enzymes. The reagents within a kit can be housed together in various combinations or can be packaged in separate vials or containers. The kits provided herein can also include labels or packaging inserts setting out instructions for preparation and use.

EXAMPLES

Example 1

Generation of Fluoride-Resistant Ureases

Material and Methods

The plasmids pKAU17 and pKAUDEFG, encoding the *Klebsiella aerogenes* urease structural genes and accessory genes respectively, were donated by Dr. Scott Mulrooney of the University of Michigan, Lansing. *E. coli* strains used in these experiments were DH10B (Invitrogen) and XL1-red (Stratagene). DH10B was used as the screening and cloning host for the plasmids; XL1-red was used for mutagenesis only. The cloning vector used for these experiments was pCM66, a dual replicon, broad host range, mobilizable, kanamycin-resistant plasmid (Marx and Lindstrom, (2001) Microbiology 147: 2065-2075). Growth media were Luria agar (LA), Luria agar/broth+0.4 mM $NiCl_2$ (LAnick or LBnick) or M9 modified urea agar or broth (M9 Mod Urea). Antibiotic selection for the plasmids was 50 μg/ml ampicillin (pKAUDEFG or pKAU17) and/or 25 μg/ml kanamycin (pCM66-derived plasmids). Bluogal was added to the LA to provide blue/white color screening needed for recombinant plasmid identification. Screening solution was 0.1-0.2 M sodium fluoride in 0.5-1.25 mM HEPES, pH 7, 55 μg/ml phenol red, 10 mM HEPES. Pre-inhibition solution for the screening was 0.5-1.25 mM HEPES, pH 7, 0.1 M sodium fluoride. Screening filters were 82 mm nitrocellulose circles. Screening pads were VWR 283 (Ahlstrom) cut to size.

Mutagenesis of pABC9

The ureABC structural genes were subcloned from the plasmid pKAU17 into the pCM66 vector to produce the plasmid pABC9. The pABC9 plasmid encoding the urease genes (SEQ ID NO:7) was transformed into competent XL1-red cells (Stratagene). The cells were spread onto LA Kan25 and incubated for 48 hours at 37° C. The colonies were scraped from the plates and the plasmids extracted using the Wizard SV procedure (Promega). Putative mutant urease structural genes were removed from the extracted plasmids by restriction endonuclease digestion, isolated by agarose gel electrophoresis, extracted from the agarose gel and recloned into fresh unmutated cloning vector prior to screening.

Screening of Mutagenized pABC9

The mutagenized plasmids were co-transformed with pKAUDEFG into Electromax DH10B, diluted and spread onto forty LAnick Kan25 Amp50 plates. After overnight incubation at 37° C., the colonies were lifted from the plates with numbered nitrocellulose filters. The filters were placed colony side up into the bottom of water-dampened glass Petri dishes. The lifted plates were returned to 37° C. to re-grow the colonies. The colonies on the filters were lysed with 2 ml of chloroform in the lids of the inverted glass Petri dishes for 30 minutes. The lids were removed from the plates and the residual chloroform evaporated for 2 minutes in a fume hood. The filters were laid on pads soaked with pre-inhibition solution for 10 minutes at room temperature in a large screening box. After pre-inhibition, the filters were transferred to pads soaked with the assay solution in another large screening box. The pink color development was noted at room temperature from 30 seconds to 10 minutes. Lysed, Urease-positive colonies were tracked via number and location on the filters to the corresponding plates.

After the colonies re-grew on the lifted plates from above, the positive colonies were picked and patched onto LAnick Kan25 Amp50 plates. The patched plates were incubated overnight at 37° C. The original patch plate was replica plated with velveteen onto three LAnick Kan25 Amp50 plates. After overnight growth, the replicated patches were lifted from plates with filters, lysed and assayed in the same manner described above but assayed in individual polystyrene plates instead of the large box. The assay solution used for this analysis varied in the fluoride (0.1-0.2) and in the buffer (0.5-1.25 mM HEPES) concentration to detect the best activity of the patched clones.

Capture of Single Plasmid Clones from Double Plasmid Clones

The pABC9 mutant plasmids were recovered from the double plasmid clones resulting from the fluoride-resistance screening by clipped transformation. Plasmid DNA was purified from individual fluoride-resistant colonies and digested with the restriction enzyme, ScaI, which cuts once in pKAUDEFG but not in pABC9. The digests were transformed into competent DH10B cells and the transformed cells plated on LA Kan25. Colonies obtained from this transformation were tested for the absence of the pKAUDEFG plasmid by picking and patching them onto LA Amp50 plates and inoculating them into M9 mod urea Kan25 Broth. Colonies with the Kanamycin-resistant, Ampicillin-sensitive phenotype were inoculated into 5 ml of LA Kan25, shaken overnight at 37° C., harvested, and plasmids prepared from the cells using the Wizard SV procedure. Restriction endonuclease digestion of the plasmid preparations with BamHI or EcoRI-HindIII and subsequent agarose gel electrophoresis were used to confirm the presence of the sole pABC9-descendant plasmids.

Example 2

Activity of Fluoride Resistant Ureases

Intracellular Extract Analysis

Urease enzymes were partially purified by anion exchange chromatography and size exclusion. Enzymes were preincubated in the fluoride concentrations indicated for 10 minutes prior to initiating the reaction with urea (10 mM final concentration). Reaction temperature was 25° C. A comparison of the activity of the fluoride-resistant mutant enzymes with the wild-type activity is shown in Table 1. The mutant urease enzymes, 9-1 and 10-1, had many times the urease activity of parental enzyme at NaF concentrations that ranged from 5-50 mM.

TABLE I

Urease activity in wild-type and mutant ureases.*

| | Enzyme | | |
|---|---|---|---|
| [NaF] mM | Wild-type | Mutant 9-1 | Mutant 10-1 |
| 0 | 171.49 | 3412.67 | 91.32 |
| 5 | 2.22 | 52.44 | 38.21 |
| 10 | 0.77 | 35.33 | 28.15 |
| 20 | 0.23 | 7.13 | 17.41 |
| 50 | 0.12 | 2.38 | 8.82 |

*Values represent specific activity as μmoles urea hydrolyzed/min/mg protein, corrected for percent urease in the sample.

Example 3

Nucleotide Sequences of Fluoride Resistant Ureases

The parental ureABC and the mutant urease genes were sequenced; alignment of the DNA sequences of the parental (KAU) (SEQ ID NO:7), 9-1 (SEQ ID NO:8) and 10-1 (SEQ ID NO:9) mutant urease ureABC genes is shown in FIG. 1. Gene regions for the urease subunits include: ureA, encoded by nucleotides 1-303; ureB, encoded by nucleotides 313-633; ureC, encoded by nucleotides 626-2329. Mutations were located in the ureC gene, which encodes the alpha subunit of the enzyme. Mutant urease 9-1 had a substitution of an adenosine for guanine at position 1553 of SEQ ID NO:7 (i.e. at position 928 of SEQ ID NO: 2, which represents the nucleotide sequence of only the alpha subunit). Mutant urease 10-1, in addition to having a substitution of an adenosine for guanine at position 1553 of SEQ ID NO:7 (i.e. at position 928 of SEQ ID NO: 2, which represents the nucleotide sequence of only the alpha subunit), also had an additional substitution of an adenosine for a guanine at position 1570 of SEQ ID NO:7 (i.e. at position 945 of SEQ ID NO:2 which represents the nucleotide sequence of only the alpha subunit).

Example 4

Comparative Amino Acid Sequences of Fluoride Resistant Ureases

A conceptual translation of the ureC gene for the parental and mutant ureases was performed. FIG. 2 shows an alignment of the alpha subunit amino acid sequences encoded by the ureC genes of the parental (KAU) (SEQ ID NO:1), 9-1 (SEQ ID NO:5) and 10-1 (SEQ ID NO:6) mutant ureases. The mutation at position 1553 in the nucleotide sequence of SEQ ID NO:7 (i.e. at position 928 of SEQ ID NO: 2, which represents the nucleotide sequence of only the alpha subunit) resulted in the substitution of asparagine for aspartic acid at amino acid 310 in mutant enzymes 9-1 (SEQ ID NO:5) and 10-1 (SEQ ID NO:6). The mutation at position 1570 of SEQ ID NO:7 (i.e. at position 945 of SEQ ID NO:2 which represents the nucleotide sequence of only the alpha subunit) in the nucleotide sequence in the 10-1 enzyme resulted in an additional substitution of an isoleucine residue for the methionine residue at position 315 (SEQ ID NO:6).

Example 5

Effect of Fluoride-Resistant Urease on OPAA-Catalysed DFP Hydrolysis

The effect of mutant urease-mediated catalytic buffering in a fluoride generating reaction was evaluated by adding the mutant urease 9-1 to reactions that contained the Sarin-hydrolyzing enzyme, organophosphorus anhydrolase (OPAA) from *Alteromonas* sp. JD6.6.

The OPAA substrate was the sarin-simulant diisopropylphosphorfluoridate (DFP). In this experiment, the value for the OPAA activity in the presence of 50 mM ammonium carbonate buffer was set at 100%. The results presented in Table II show that the same activity was obtained when the 9-1 urease plus 10 mM urea was substituted for the ammonium carbonate. Furthermore, the observed catalytic rate of the reaction doubled when the urease/urea combination was used in addition to the ammonium carbonate.

TABLE II

Effect of 9-1 urease on OPAA-catalyzed DFP hydrolysis.*

| Reaction Component | | | | |
|---|---|---|---|---|
| OPAA (16 μg/ml) | Urease (3 units) | Ammonium carbonate (5 mM) | Urea (50 mM) | Percent relative activity |
| + | − | + | − | 100 |
| − | + | + | + | 40.3 |
| + | + | − | + | 100.6 |
| + | + | + | + | 200.8 |

*DFP concentration was 3 mM; reaction temperature was 25° C.

Example 6

Time-Course Analyses of Catalytic Buffering by Fluoride Resistant Urease on OPAA-Catalyzed DFP Hydrolysis During the course of OPAA-catalyzed DFP hydrolysis, the fluoride concentration increases and the pH decreases. The ability of the mutant ureases to maintain a steady pH in the face of increasing fluoride concentrations that are a function of OPAA-catalyzed hydrolysis of organophosphate molecules was evaluated in a time-course assay. For this experiment, the 9-1 urease (1.5 units/mL) was added to a reaction that included 16 μg/mL of OPAA, 3 mM DFP and 5 mM ammonium carbonate in either the presence or absence of 10 mM urea. The pH of the reaction was assayed at intervals over the course of 35 minutes. The results shown in FIG. 3 indicate that in the absence of urease activity, the pH of the reaction fell steadily from the starting pH of about 8.6 to below 7.4. In the presence of urease activity, a steady pH at or near the pH optimum for OPAA of 8.5 was maintained over the course of the experiment.

Figure 4:
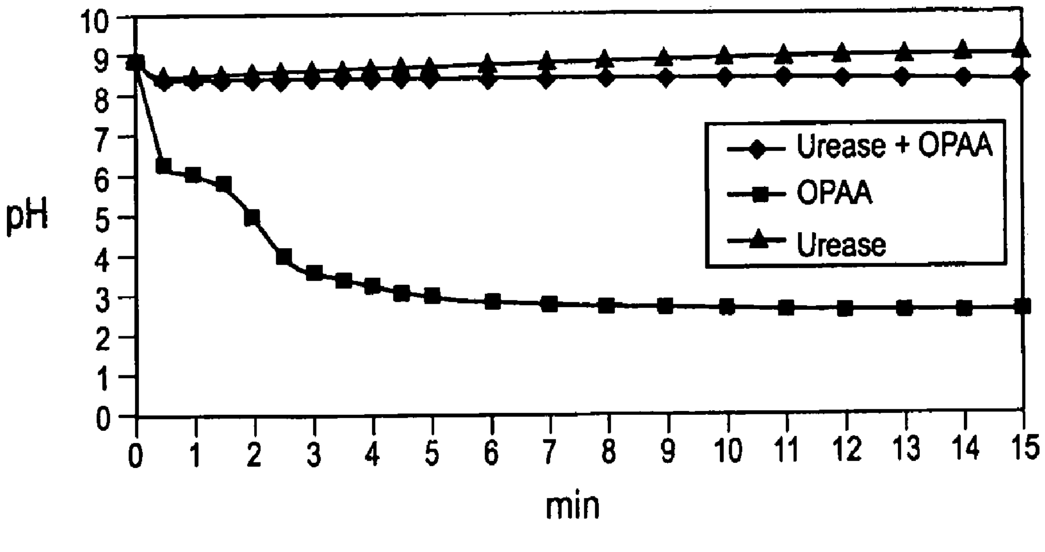
FIG. 4 shows catalytic buffering of organophosphorus acid anhydrolase (OPAA) reactions with a combination of 9-1 and 10-1 ureases at a high substrate concentration. Reactions contained 5 mM ammonium carbonate, 110 mM DFP, 250 mM urea and enzymes as indicated (diamond symbols: ureases plus OPAA; square symbols: OPAA alone; triangle symbols: ureases alone.). The urease concentrations were 6.06 and 0.37 units per/mL of 9-1 and 10-1 respectively and 16 µg/mL of OPAA. Reaction temperature was 25° C.

The catalytic buffering efficacy of the mutant ureases was also measured in the presence of high concentrations of DFP. For this experiment, the pH was monitored over time in reactions that contained either OPAA alone, OPAA plus urease or urease alone. Urease activity was provided by a mixture of mutant ureases, 9-1 at 6.06 units/mL, and 10-1 at 0.37 units/mL, since the former had shown better activity at lower fluoride concentrations (<25 mM) while the latter was more active at higher fluoride concentrations (>25 mM). The OPAA concentration was 16 μg/mL. All reactions contained 5 mM ammonium carbonate, 110 mM DFP and 250 mM urea. The pH of the reaction was assayed at intervals over the course of 15 minutes. The results shown in FIG. 4 indicate that in the absence of urease (square symbols) the pH of the reaction fell within 5 minutes to below pH 3.0; in the presence of urease a steady pH at or near the pH optimum for OPAA of 8.5 was maintained over the course of the experiment (diamond symbols and triangle symbols).

A number of embodiments of the invention have been described. Nevertheless, it will be understood that various modifications may be made without departing from the spirit and scope of the invention. Accordingly, other embodiments are within the scope of the following claims.

What is claimed is:

1. An isolated nucleic acid comprising a nucleotide sequence encoding a mutated alpha subunit polypeptide of an urease holoenzyme wherein the holoenzyme is resistant to fluoride when it comprises the mutated alpha subunit, and wherein said alpha subunit polypeptide is from the organism *Klebsiella aerogenes*, and wherein said nucleotide sequence encodes the amino acid sequence shown in SEQ ID NO: 5.

2. The isolated nucleic acid of claim 1, wherein said nucleotide sequence is the sequence set forth in SEQ ID NO: 3, said sequence having a mutation consisting of an adenosine residue at position 928 in SEQ ID NO: 3.

3. An isolated nucleic acid comprising a nucleotide sequence encoding a mutated alpha subunit polypeptide of an urease holoenzyme wherein the holoenzyme is resistant to fluoride when it comprises the mutated alpha subunit, and wherein said alpha subunit polypeptide is from the organism *Klebsiella aerogenes*, and wherein said nucleotide sequence encodes the amino acid sequence shown in SEQ ID NO: 6.

4. The isolated nucleic acid of claim 3, wherein said nucleotide sequence is the sequence set forth in SEQ ID NO: 4, said sequence having a mutation consisting of an adenosine residue at position 928 and an adenosine residue at position 945 of SEQ ID NO: 4.

5. A recombinant DNA construct for expressing a mutated alpha subunit of a urease holoenzyme endogenous to *Klebsiella aerogenes* in prokaryotic cells, said construct comprising a prokaryotic promoter operably linked to a DNA molecule selected from the group consisting of SEQ ID: NO 3 and SEQ ID NO: 4.

6. The recombinant DNA construct of claim 5, wherein the DNA molecule is SEQ ID NO: 3.

7. The recombinant DNA construct of claim 5, wherein the DNA molecule is SEQ ID NO: 4.

8. A recombinant microorganism comprising a host cell transformed by the recombinant DNA construct of claim 5.

9. The recombinant microorganism of claim 8, wherein said host cell expresses urease structural and accessory genes for the synthesis of enzymatically active urease holoenzyme.

* * * * *

SEQUENCE LISTING

```
<160> NUMBER OF SEQ ID NOS: 9

<210> SEQ ID NO 1
<211> LENGTH: 567
```

-continued

<212> TYPE: PRT
<213> ORGANISM: Klebsiella aerogenes

<400> SEQUENCE: 1

```
Met Ser Asn Ile Ser Arg Gln Ala Tyr Ala Asp Met Phe Gly Pro Thr
 1               5                  10                  15

Val Gly Asp Lys Val Arg Leu Ala Asp Thr Glu Leu Trp Ile Glu Val
            20                  25                  30

Glu Asp Asp Leu Thr Thr Tyr Gly Glu Glu Val Lys Phe Gly Gly Gly
        35                  40                  45

Lys Val Ile Arg Asp Gly Met Gly Gln Gly Gln Met Leu Ala Ala Asp
    50                  55                  60

Cys Val Asp Leu Val Leu Thr Asn Ala Leu Ile Val Asp His Trp Gly
65                  70                  75                  80

Ile Val Lys Ala Asp Ile Gly Val Lys Asp Gly Arg Ile Phe Ala Ile
                85                  90                  95

Gly Lys Ala Gly Asn Pro Asp Ile Gln Pro Asn Val Thr Ile Pro Ile
            100                 105                 110

Gly Ala Ala Thr Glu Val Ile Ala Ala Glu Gly Lys Ile Val Thr Ala
        115                 120                 125

Gly Gly Ile Asp Thr His Ile His Trp Ile Cys Pro Gln Gln Ala Glu
    130                 135                 140

Glu Ala Leu Val Ser Gly Val Thr Thr Met Val Gly Gly Gly Thr Gly
145                 150                 155                 160

Pro Ala Ala Gly Thr His Ala Thr Thr Cys Thr Pro Gly Pro Trp Tyr
                165                 170                 175

Ile Ser Arg Met Leu Gln Ala Ala Asp Ser Leu Pro Val Asn Ile Gly
            180                 185                 190

Leu Leu Gly Lys Gly Asn Val Ser Gln Pro Asp Ala Leu Arg Glu Gln
        195                 200                 205

Val Ala Ala Gly Val Ile Gly Leu Lys Ile His Glu Asp Trp Gly Ala
    210                 215                 220

Thr Pro Ala Ala Ile Asp Cys Ala Leu Thr Val Ala Asp Glu Met Asp
225                 230                 235                 240

Ile Gln Val Ala Leu His Ser Asp Thr Leu Asn Glu Ser Gly Phe Val
                245                 250                 255

Glu Asp Thr Leu Ala Ala Ile Gly Gly Arg Thr Ile His Thr Phe His
            260                 265                 270

Thr Glu Gly Ala Gly Gly Gly His Ala Pro Asp Ile Ile Thr Ala Cys
        275                 280                 285

Ala His Pro Asn Ile Leu Pro Ser Ser Thr Asn Pro Thr Leu Pro Tyr
    290                 295                 300

Thr Leu Asn Thr Ile Asp Glu His Leu Asp Met Leu Met Val Cys His
305                 310                 315                 320

His Leu Asp Pro Asp Ile Ala Glu Asp Val Ala Phe Ala Glu Ser Arg
                325                 330                 335

Ile Arg Arg Glu Thr Ile Ala Ala Glu Asp Val Leu His Asp Leu Gly
            340                 345                 350

Ala Phe Ser Leu Thr Ser Ser Asp Ser Gln Ala Met Gly Arg Val Gly
        355                 360                 365

Glu Val Ile Leu Arg Thr Trp Gln Val Ala His Arg Met Lys Val Gln
    370                 375                 380

Arg Gly Ala Leu Ala Glu Glu Thr Gly Asp Asn Asp Asn Phe Arg Val
385                 390                 395                 400
```

-continued

```
Lys Arg Tyr Ile Ala Lys Tyr Thr Ile Asn Pro Ala Leu Thr His Gly
                405                 410                 415

Ile Ala His Glu Val Gly Ser Ile Glu Val Gly Lys Leu Ala Asp Leu
            420                 425                 430

Val Val Trp Ser Pro Ala Phe Phe Gly Val Lys Pro Ala Thr Val Ile
        435                 440                 445

Lys Gly Gly Met Ile Ala Ile Ala Pro Met Gly Asp Ile Asn Ala Ser
    450                 455                 460

Ile Pro Thr Pro Gln Pro Val His Tyr Arg Pro Met Phe Gly Ala Leu
465                 470                 475                 480

Gly Ser Ala Arg His His Cys Arg Leu Thr Phe Leu Ser Gln Ala Ala
                485                 490                 495

Ala Ala Asn Gly Val Ala Glu Arg Leu Asn Leu Arg Ser Ala Ile Ala
            500                 505                 510

Val Val Lys Gly Cys Arg Thr Val Gln Lys Ala Asp Met Val His Asn
        515                 520                 525

Ser Leu Gln Pro Asn Ile Thr Val Asp Ala Gln Thr Tyr Glu Val Arg
    530                 535                 540

Val Asp Gly Glu Leu Ile Thr Ser Glu Pro Ala Asp Val Leu Pro Met
545                 550                 555                 560

Ala Gln Arg Tyr Phe Leu Phe
                565


<210> SEQ ID NO 2
<211> LENGTH: 1704
<212> TYPE: DNA
<213> ORGANISM: Klebsiella aerogenees

<400> SEQUENCE: 2

atgagtaata tttcacgcca ggcctatgcc gatatgttcg gccccaccgt cggcgacaag      60

gtgcgcctgg cagataccga gctgtggatc gaggtggagg acgatttgac cacctacggg     120

gaagaggtca aattcggcgg cggcaaagtg atccgcgacg gcatgggcca gggacagatg     180

ctggccgccg actgtgtcga cctggtgctc accaacgcgt tgatcgtcga tcactggggg     240

atcgttaagg ccgatatcgg cgtgaaggac ggccggatct tcgccatcgg caaagccggc     300

aaccccgaca tccagcccaa cgtcaccatc cccatcggcg ctgcgacgga agtgatcgcc     360

gccgaaggaa aaattgtcac cgccggcggg atcgataccc atattcactg gatctgtccg     420

cagcaggcgg aagaggcgct ggtctctggc gtgaccacca tggtcggcgg cggcaccggc     480

ccggccgcgg gcacccatgc caccacctgc accccgggcc cgtggtatat ctcacgcatg     540

ctgcaggcgg ccgacagcct gccggtcaat atcggcctgc tgggcaaggg aaacgtttct     600

cagccggatg ccctgcgcga gcaggtggcg gcaggcgtta ttggcctgaa gatccatgag     660

gactggggcg ccaccccggc ggcgatcgac tgtgcgttaa ccgtcgccga tgaaatggac     720

atccaggtcg ccctgcacag cgacaccctg aatgaatccg gttttgtgga agacaccctc     780

gccgccatcg gcgggcgcac catccacacc ttccataccg aaggggccgg cggcggccat     840

gcgccggaca tcatcaccgc ctgcgcccac ccgaacattt tgccgtcgtc caccaaccca     900

acgctgccct acaccctcaa caccatcgat gaacatctcg atatgctgat ggtctgccac     960

catctggacc cggacatcgc cgaggacgtg gcctttgccg agtcgcgcat tcgccgggaa    1020

accatcgctg cggaagacgt gctgcacgat ctcggcgcct tctcgctcac ctcctccgat    1080

tcgcaggcca tgggccgcgt cggggaagtg attctccgca cctggcaggt ggcgcatcgc    1140
```

-continued atgaaggtgc agcgcggagc gctggcggag gagaccgggg ataacgacaa cttccgcgtg 1200
aagcgctaca tcgccaaata caccatcaac ccggcgctga cccacggcat cgcacacgaa 1260
gtcggatcca ttgaggtggg taagctggct gacctcgtgg tctggtcacc agccttcttc 1320
ggcgtgaaac cggccaccgt gatcaaaggc ggcatgatcg ccatcgcgcc gatgggcgat 1380
atcaatgcct ctattccgac cccgcagccg gtgcactacc gcccgatgtt tggcgcgctg 1440
ggcagcgccc gccatcactg ccgcctcacc ttcctgtcgc aggcggcggc agccaatggc 1500
gttgccgagc ggctgaacct gcgcagcgcg atcgccgtgg tgaaaggctg ccgtacggtg 1560
cagaaagccg acatggtgca caacagtctg cagcctaaca tcaccgtcga cgcccagacc 1620
tatgaggtgc gggtggatgg cgaacttatc accagcgagc cggcagacgt tctgccgatg 1680
gcgcaacgat attttctgtt ttaa 1704

<210> SEQ ID NO 3
<211> LENGTH: 1704
<212> TYPE: DNA
<213> ORGANISM: Klebsiella aerogenes

<400> SEQUENCE: 3
atgagtaata tttcacgcca ggcctatgcc gatatgttcg gccccaccgt cggcgacaag 60
gtgcgcctgg cagataccga gctgtggatc gaggtggagg acgatttgac cacctacggg 120
gaagaggtca aattcggcgg cggcaaagtg atccgcgacg gcatgggcca gggacagatg 180
ctggccgccg actgtgtcga cctggtgctc accaacgcgt tgatcgtcga tcactggggg 240
atcgttaagg ccgatatcgg cgtgaaggac ggccggatct tcgccatcgg caaagccggc 300
aaccccgaca tccagcccaa cgtcaccatc cccatcggcg ctgcgacgga agtgatcgcc 360
gccgaaggaa aaattgtcac cgccggcggg atcgataccc atattcactg gatctgtccg 420
cagcaggcgg aagaggcgct ggtctctggc gtgaccacca tggtcggcgg cggcaccggc 480
ccggccgcgg gcacccatgc caccacctgc accccgggcc cgtggtatat ctcacgcatg 540
ctgcaggcgg ccgacagcct gccggtcaat atcggcctgc tgggcaaggg aaacgtttct 600
cagccggatg ccctgcgcga gcaggtggcg gcaggcgtta ttggcctgaa gatccatgag 660
gactggggcg ccaccccggc ggcgatcgac tgtgcgttaa ccgtcgccga tgaaatggac 720
atccaggtcg ccctgcacag cgacaccctg aatgaatccg gttttgtgga agacaccctc 780
gccgccatcg gcgggcgcac catccacacc ttccataccg aaggggccgg cggcggccat 840
gcgccggaca tcatcaccgc ctgcgcccac ccgaacattt tgccgtcgtc caccaaccca 900
acgctgccct acaccctcaa caccatcaat gaacatctcg atatgctgat ggtctgccac 960
catctggacc cggacatcgc cgaggacgtg gcctttgccg agtcgcgcat tcgccgggaa 1020
accatcgctg cggaagacgt gctgcacgat ctcggcgcct tctcgctcac ctcctccgat 1080
tcgcaggcca tgggccgcgt cggggaagtg attctccgca cctggcaggt ggcgcatcgc 1140
atgaaggtgc agcgcggagc gctggcggag gagaccgggg ataacgacaa cttccgcgtg 1200
aagcgctaca tcgccaaata caccatcaac ccggcgctga cccacggcat cgcacacgaa 1260
gtcggatcca ttgaggtggg taagctggct gacctcgtgg tctggtcacc agccttcttc 1320
ggcgtgaaac cggccaccgt gatcaaaggc ggcatgatcg ccatcgcgcc gatgggcgat 1380
atcaatgcct ctattccgac cccgcagccg gtgcactacc gcccgatgtt tggcgcgctg 1440
ggcagcgccc gccatcactg ccgcctcacc ttcctgtcgc aggcggcggc agccaatggc 1500

-continued gttgccgagc ggctgaacct gcgcagcgcg atcgccgtgg tgaaaggctg ccgtacggtg 1560
cagaaagccg acatggtgca caacagtctg cagcctaaca tcaccgtcga cgcccagacc 1620
tatgaggtgc gggtggatgg cgaacttatc accagcgagc cggcagacgt tctgccgatg 1680
gcgcaacgat attttctgtt ttaa 1704

<210> SEQ ID NO 4
<211> LENGTH: 1704
<212> TYPE: DNA
<213> ORGANISM: Klebsiella aerogenes

<400> SEQUENCE: 4
atgagtaata tttcacgcca ggcctatgcc gatatgttcg gccccaccgt cggcgacaag 60
gtgcgcctgg cagataccga gctgtggatc gaggtggagg acgatttgac cacctacggg 120
gaagaggtca aattcggcgg cggcaaagtg atccgcgacg gcatgggcca gggacagatg 180
ctggccgccg actgtgtcga cctggtgctc accaacgcgt tgatcgtcga tcactggggg 240
atcgttaagg ccgatatcgg cgtgaaggac ggccggatct tcgccatcgg caaagccggc 300
aaccccgaca tccagcccaa cgtcaccatc cccatcggcg ctgcgacgga agtgatcgcc 360
gccgaaggaa aaattgtcac cgccggcggg atcgataccc atattcactg gatctgtccg 420
cagcaggcgg aagaggcgct ggtctctggc gtgaccacca tggtcggcgg cggcaccggc 480
ccggccgcgg gcacccatgc caccacctgc accccgggcc cgtggtatat ctcacgcatg 540
ctgcaggcgg ccgacagcct gccggtcaat atcggcctgc tgggcaaggg aaacgtttct 600
cagccggatg ccctgcgcga gcaggtggcg gcaggcgtta ttggcctgaa gatccatgag 660
gactggggcg ccacccccggc ggcgatcgac tgtgcgttaa ccgtcgccga tgaaatggac 720
atccaggtcg ccctgcacag cgacaccctg aatgaatccg gttttgtgga agacaccctc 780
gccgccatcg gcgggcgcac catccacacc ttccataccg aaggggccgg cggcggccat 840
gcgccggaca tcatcaccgc ctgcgcccac ccgaacattt tgccgtcgtc caccaaccca 900
acgctgccct acaccctcaa caccatcaat gaacatctcg atatactgat ggtctgccac 960
catctggacc cggacatcgc cgaggacgtg gcctttgccg agtcgcgcat tcgccgggaa 1020
accatcgctg cggaagacgt gctgcacgat ctcggcgcct tctcgctcac ctcctccgat 1080
tcgcaggcca tgggccgcgt cggggaagtg attctccgca cctggcaggt ggcgcatcgc 1140
atgaaggtgc agcgcggagc gctggcggag gagaccgggg ataacgacaa cttccgcgtg 1200
aagcgctaca tcgccaaata caccatcaac ccggcgctga cccacggcat cgcacacgaa 1260
gtcggatcca ttgaggtggg taagctggct gacctcgtgg tctggtcacc agccttcttc 1320
ggcgtgaaac cggccaccgt gatcaaaggc ggcatgatcg ccatcgcgcc gatgggcgat 1380
atcaatgcct ctattccgac cccgcagccg gtgcactacc gcccgatgtt tggcgcgctg 1440
ggcagcgccc gccatcactg ccgcctcacc ttcctgtcgc aggcggcggc agccaatggc 1500
gttgccgagc ggctgaacct gcgcagcgcg atcgccgtgg tgaaaggctg ccgtacggtg 1560
cagaaagccg acatggtgca caacagtctg cagcctaaca tcaccgtcga cgcccagacc 1620
tatgaggtgc gggtggatgg cgaacttatc accagcgagc cggcagacgt tctgccgatg 1680
gcgcaacgat attttctgtt ttaa 1704

<210> SEQ ID NO 5
<211> LENGTH: 567
<212> TYPE: PRT
<213> ORGANISM: Klebsiella aerogenes -continued

<400> SEQUENCE: 5

Met Ser Asn Ile Ser Arg Gln Ala Tyr Ala Asp Met Phe Gly Pro Thr
1 5 10 15

Val Gly Asp Lys Val Arg Leu Ala Asp Thr Glu Leu Trp Ile Glu Val
20 25 30

Glu Asp Asp Leu Thr Thr Tyr Gly Glu Glu Val Lys Phe Gly Gly Gly
35 40 45

Lys Val Ile Arg Asp Gly Met Gly Gln Gly Gln Met Leu Ala Ala Asp
50 55 60

Cys Val Asp Leu Val Leu Thr Asn Ala Leu Ile Val Asp His Trp Gly
65 70 75 80

Ile Val Lys Ala Asp Ile Gly Val Lys Asp Gly Arg Ile Phe Ala Ile
85 90 95

Gly Lys Ala Gly Asn Pro Asp Ile Gln Pro Asn Val Thr Ile Pro Ile
100 105 110

Gly Ala Ala Thr Glu Val Ile Ala Ala Glu Gly Lys Ile Val Thr Ala
115 120 125

Gly Gly Ile Asp Thr His Ile His Trp Ile Cys Pro Gln Gln Ala Glu
130 135 140

Glu Ala Leu Val Ser Gly Val Thr Thr Met Val Gly Gly Gly Thr Gly
145 150 155 160

Pro Ala Ala Gly Thr His Ala Thr Thr Cys Thr Pro Gly Pro Trp Tyr
165 170 175

Ile Ser Arg Met Leu Gln Ala Ala Asp Ser Leu Pro Val Asn Ile Gly
180 185 190

Leu Leu Gly Lys Gly Asn Val Ser Gln Pro Asp Ala Leu Arg Glu Gln
195 200 205

Val Ala Ala Gly Val Ile Gly Leu Lys Ile His Glu Asp Trp Gly Ala
210 215 220

Thr Pro Ala Ala Ile Asp Cys Ala Leu Thr Val Ala Asp Glu Met Asp
225 230 235 240

Ile Gln Val Ala Leu His Ser Asp Thr Leu Asn Glu Ser Gly Phe Val
245 250 255

Glu Asp Thr Leu Ala Ala Ile Gly Gly Arg Thr Ile His Thr Phe His
260 265 270

Thr Glu Gly Ala Gly Gly Gly His Ala Pro Asp Ile Ile Thr Ala Cys
275 280 285

Ala His Pro Asn Ile Leu Pro Ser Ser Thr Asn Pro Thr Leu Pro Tyr
290 295 300

Thr Leu Asn Thr Ile Asn Glu His Leu Asp Met Leu Met Val Cys His
305 310 315 320

His Leu Asp Pro Asp Ile Ala Glu Asp Val Ala Phe Ala Glu Ser Arg
325 330 335

Ile Arg Arg Glu Thr Ile Ala Ala Glu Asp Val Leu His Asp Leu Gly
340 345 350

Ala Phe Ser Leu Thr Ser Ser Asp Ser Gln Ala Met Gly Arg Val Gly
355 360 365

Glu Val Ile Leu Arg Thr Trp Gln Val Ala His Arg Met Lys Val Gln
370 375 380

Arg Gly Ala Leu Ala Glu Glu Thr Gly Asp Asn Asp Asn Phe Arg Val
385 390 395 400

Lys Arg Tyr Ile Ala Lys Tyr Thr Ile Asn Pro Ala Leu Thr His Gly

-continued

```
                405                 410                 415

Ile Ala His Glu Val Gly Ser Ile Glu Val Gly Lys Leu Ala Asp Leu
            420                 425                 430

Val Val Trp Ser Pro Ala Phe Phe Gly Val Lys Pro Ala Thr Val Ile
        435                 440                 445

Lys Gly Gly Met Ile Ala Ile Ala Pro Met Gly Asp Ile Asn Ala Ser
    450                 455                 460

Ile Pro Thr Pro Gln Pro Val His Tyr Arg Pro Met Phe Gly Ala Leu
465                 470                 475                 480

Gly Ser Ala Arg His His Cys Arg Leu Thr Phe Leu Ser Gln Ala Ala
                485                 490                 495

Ala Ala Asn Gly Val Ala Glu Arg Leu Asn Leu Arg Ser Ala Ile Ala
            500                 505                 510

Val Val Lys Gly Cys Arg Thr Val Gln Lys Ala Asp Met Val His Asn
        515                 520                 525

Ser Leu Gln Pro Asn Ile Thr Val Asp Ala Gln Thr Tyr Glu Val Arg
    530                 535                 540

Val Asp Gly Glu Leu Ile Thr Ser Glu Pro Ala Asp Val Leu Pro Met
545                 550                 555                 560

Ala Gln Arg Tyr Phe Leu Phe
                565


<210> SEQ ID NO 6
<211> LENGTH: 567
<212> TYPE: PRT
<213> ORGANISM: Klebsiella aerogenes

<400> SEQUENCE: 6

Met Ser Asn Ile Ser Arg Gln Ala Tyr Ala Asp Met Phe Gly Pro Thr
 1               5                  10                  15

Val Gly Asp Lys Val Arg Leu Ala Asp Thr Glu Leu Trp Ile Glu Val
            20                  25                  30

Glu Asp Asp Leu Thr Thr Tyr Gly Glu Glu Val Lys Phe Gly Gly Gly
        35                  40                  45

Lys Val Ile Arg Asp Gly Met Gly Gln Gly Gln Met Leu Ala Ala Asp
    50                  55                  60

Cys Val Asp Leu Val Leu Thr Asn Ala Leu Ile Val Asp His Trp Gly
65                  70                  75                  80

Ile Val Lys Ala Asp Ile Gly Val Lys Asp Gly Arg Ile Phe Ala Ile
                85                  90                  95

Gly Lys Ala Gly Asn Pro Asp Ile Gln Pro Asn Val Thr Ile Pro Ile
            100                 105                 110

Gly Ala Ala Thr Glu Val Ile Ala Ala Glu Gly Lys Ile Val Thr Ala
        115                 120                 125

Gly Gly Ile Asp Thr His Ile His Trp Ile Cys Pro Gln Gln Ala Glu
    130                 135                 140

Glu Ala Leu Val Ser Gly Val Thr Thr Met Val Gly Gly Gly Thr Gly
145                 150                 155                 160

Pro Ala Ala Gly Thr His Ala Thr Thr Cys Thr Pro Gly Pro Trp Tyr
                165                 170                 175

Ile Ser Arg Met Leu Gln Ala Ala Asp Ser Leu Pro Val Asn Ile Gly
            180                 185                 190

Leu Leu Gly Lys Gly Asn Val Ser Gln Pro Asp Ala Leu Arg Glu Gln
        195                 200                 205
```

-continued

```
Val Ala Ala Gly Val Ile Gly Leu Lys Ile His Glu Asp Trp Gly Ala
    210                 215                 220

Thr Pro Ala Ala Ile Asp Cys Ala Leu Thr Val Ala Asp Glu Met Asp
225                 230                 235                 240

Ile Gln Val Ala Leu His Ser Asp Thr Leu Asn Glu Ser Gly Phe Val
                245                 250                 255

Glu Asp Thr Leu Ala Ala Ile Gly Gly Arg Thr Ile His Thr Phe His
            260                 265                 270

Thr Glu Gly Ala Gly Gly Gly His Ala Pro Asp Ile Ile Thr Ala Cys
        275                 280                 285

Ala His Pro Asn Ile Leu Pro Ser Ser Thr Asn Pro Thr Leu Pro Tyr
    290                 295                 300

Thr Leu Asn Thr Ile Asn Glu His Leu Asp Ile Leu Met Val Cys His
305                 310                 315                 320

His Leu Asp Pro Asp Ile Ala Glu Asp Val Ala Phe Ala Glu Ser Arg
                325                 330                 335

Ile Arg Arg Glu Thr Ile Ala Ala Glu Asp Val Leu His Asp Leu Gly
            340                 345                 350

Ala Phe Ser Leu Thr Ser Ser Asp Ser Gln Ala Met Gly Arg Val Gly
        355                 360                 365

Glu Val Ile Leu Arg Thr Trp Gln Val Ala His Arg Met Lys Val Gln
    370                 375                 380

Arg Gly Ala Leu Ala Glu Glu Thr Gly Asp Asn Asp Asn Phe Arg Val
385                 390                 395                 400

Lys Arg Tyr Ile Ala Lys Tyr Thr Ile Asn Pro Ala Leu Thr His Gly
                405                 410                 415

Ile Ala His Glu Val Gly Ser Ile Glu Val Gly Lys Leu Ala Asp Leu
            420                 425                 430

Val Val Trp Ser Pro Ala Phe Phe Gly Val Lys Pro Ala Thr Val Ile
        435                 440                 445

Lys Gly Gly Met Ile Ala Ile Ala Pro Met Gly Asp Ile Asn Ala Ser
    450                 455                 460

Ile Pro Thr Pro Gln Pro Val His Tyr Arg Pro Met Phe Gly Ala Leu
465                 470                 475                 480

Gly Ser Ala Arg His His Cys Arg Leu Thr Phe Leu Ser Gln Ala Ala
                485                 490                 495

Ala Ala Asn Gly Val Ala Glu Arg Leu Asn Leu Arg Ser Ala Ile Ala
            500                 505                 510

Val Val Lys Gly Cys Arg Thr Val Gln Lys Ala Asp Met Val His Asn
        515                 520                 525

Ser Leu Gln Pro Asn Ile Thr Val Asp Ala Gln Thr Tyr Glu Val Arg
    530                 535                 540

Val Asp Gly Glu Leu Ile Thr Ser Glu Pro Ala Asp Val Leu Pro Met
545                 550                 555                 560

Ala Gln Arg Tyr Phe Leu Phe
                565
```

<210> SEQ ID NO 7
<211> LENGTH: 2329
<212> TYPE: DNA
<213> ORGANISM: Klebsiella aerogenes

<400> SEQUENCE: 7

```
atggaactga ccccccgaga aaaagacaag ctgttgctgt ttaccgccgc gctggtggcg     60
```

-continued

```
gagcgtcgcc tggcccgcgg cctgaagctc aactatccgg agtccgtggc cctgatcagc    120

gcctttatta tggaaggcgc tcgggacggc aaaagcgtgg cctcgctgat ggaggaaggc    180

cgtcacgtcc tgacccgcga gcaggtgatg gagggcgtcc cggaaatgat cccggatatc    240

caggtcgaag ccaccttccc ggacggctcg aagctggtca ccgttcacaa cccgattatc    300

tgaggtagcg ccatgatccc cggtgaatat cacgttaagc ccggtcagat agccctgaat    360

accggccggg caacctgtcg cgtggtcgtt gagaaccacg gcgatcggcc gattcaggtc    420

ggttcgcact accatttcgc cgaggttaac ccggcgctga agttcgaccg tcagcaggcc    480

gccggctatc gcctgaatat cccggcgggc acggcggtac gctttgaacc cggccagaaa    540

cgcgaggtcg agctggtggc cttcgccggt caccgcgccg tcttcggctt ccgcggcgag    600

gtcatgggcc ctctggaggt aaacgatgag taatatttca cgccaggcct atgccgatat    660

gttcggcccc accgtcggcg acaaggtgcg cctggcagat accgagctgt ggatcgaggt    720

ggaggacgat ttgaccacct acggggaaga ggtcaaattc ggcggcggca aagtgatccg    780

cgacggcatg ggccagggac agatgctggc cgccgactgt gtcgacctgg tgctcaccaa    840

cgcgttgatc gtcgatcact gggggatcgt taaggccgat atcggcgtga aggacggccg    900

gatcttcgcc atcggcaaag ccggcaaccc cgacatccag cccaacgtca ccatccccat    960

cggcgctgcg acggaagtga tcgccgccga aggaaaaatt gtcaccgccg gcgggatcga   1020

tacccatatt cactggatct gtccgcagca ggcggaagag gcgctggtct ctggcgtgac   1080

caccatggtc ggcggcggca ccggcccggc cgcgggcacc catgccacca cctgcacccc   1140

gggcccgtgg tatatctcac gcatgctgca ggcggccgac agcctgccgg tcaatatcgg   1200

cctgctgggc aagggaaacg tttctcagcc ggatgccctg cgcgagcagg tggcggcagg   1260

cgttattggc ctgaagatcc atgaggactg gggcgccacc ccggcggcga tcgactgtgc   1320

gttaaccgtc gccgatgaaa tggacatcca ggtcgccctg cacagcgaca ccctgaatga   1380

atccggtttt gtggaagaca ccctcgccgc catcggcggg cgcaccatcc acaccttcca   1440

taccgaaggg gccggcggcg gccatgcgcc ggacatcatc accgcctgcg cccacccgaa   1500

cattttgccg tcgtccacca acccaacgct gccctacacc ctcaacacca tcgatgaaca   1560

tctcgatatg ctgatggtct gccaccatct ggacccggac atcgccgagg acgtggcctt   1620

tgccgagtcg cgcattcgcc gggaaaccat cgctgcggaa gacgtgctgc acgatctcgg   1680

cgccttctcg ctcacctcct ccgattcgca ggccatgggc cgcgtcgggg aagtgattct   1740

ccgcacctgg caggtggcgc atcgcatgaa ggtgcagcgc ggagcgctgg cggaggagac   1800

cggggataac gacaacttcc gcgtgaagcg ctacatcgcc aaatacacca tcaacccggc   1860

gctgacccac ggcatcgcac acgaagtcgg atccattgag gtgggtaagc tggctgacct   1920

cgtggtctgg tcaccagcct tcttcggcgt gaaaccggcc accgtgatca aaggcggcat   1980

gatcgccatc gcgccgatgg gcgatatcaa tgcctctatt ccgaccccgc agccggtgca   2040

ctaccgcccg atgtttggcg cgctgggcag cgcccgccat cactgccgcc tcaccttcct   2100

gtcgcaggcg gcggcagcca atggcgttgc cgagcggctg aacctgcgca gcgcgatcgc   2160

cgtggtgaaa ggctgccgta cggtgcagaa agccgacatg gtgcacaaca gtctgcagcc   2220

taacatcacc gtcgacgccc agacctatga ggtgcgggtg gatggcgaac ttatcaccag   2280

cgagccggca gacgttctgc cgatggcgca acgatatttt ctgttttaa               2329
```

<210> SEQ ID NO 8
<211> LENGTH: 2329

-continued

<212> TYPE: DNA
<213> ORGANISM: Klebsiella aerogenes

<400> SEQUENCE: 8
atggaactga ccccccgaga aaaagacaag ctgttgctgt ttaccgccgc gctggtggcg 60
gagcgtcgcc tggcccgcgg cctgaagctc aactatccgg agtccgtggc cctgatcagc 120
gcctttatta tggaaggcgc tcgggacggc aaaagcgtgg cctcgctgat ggaggaaggc 180
cgtcacgtcc tgacccgcga gcaggtgatg gagggcgtcc cggaaatgat cccggatatc 240
caggtcgaag ccaccttccc ggacggctcg aagctggtca ccgttcacaa cccgattatc 300
tgaggtagcg ccatgatccc cggtgaatat cacgttaagc ccggtcagat agccctgaat 360
accggccggg caacctgtcg cgtggtcgtt gagaaccacg gcgatcggcc gattcaggtc 420
ggttcgcact accatttcgc cgaggttaac ccggcgctga agttcgaccg tcagcaggcc 480
gccggctatc gcctgaatat cccggcgggc acggcggtac gctttgaacc cggccagaaa 540
cgcgaggtcg agctggtggc cttcgccggt caccgcgccg tcttcggctt ccgcggcgag 600
gtcatgggcc ctctggaggt aaacgatgag taatatttca cgccaggcct atgccgatat 660
gttcggcccc accgtcggcg acaaggtgcg cctggcagat accgagctgt ggatcgaggt 720
ggaggacgat ttgaccacct acggggaaga ggtcaaattc ggcggcggca aagtgatccg 780
cgacggcatg ggccagggac agatgctggc cgccgactgt gtcgacctgg tgctcaccaa 840
cgcgttgatc gtcgatcact gggggatcgt taaggccgat atcggcgtga aggacggccg 900
gatcttcgcc atcggcaaag ccggcaaccc cgacatccag cccaacgtca ccatccccat 960
cggcgctgcg acggaagtga tcgccgccga aggaaaaatt gtcaccgccg gcgggatcga 1020
tacccatatt cactggatct gtccgcagca ggcggaagag gcgctggtct ctggcgtgac 1080
caccatggtc ggcggcggca ccggcccggc cgcgggcacc catgccacca cctgcacccc 1140
gggcccgtgg tatatctcac gcatgctgca ggcggccgac agcctgccgg tcaatatcgg 1200
cctgctgggc aagggaaacg tttctcagcc ggatgccctg cgcgagcagg tggcggcagg 1260
cgttattggc ctgaagatcc atgaggactg gggcgccacc ccggcggcga tcgactgtgc 1320
gttaaccgtc gccgatgaaa tggacatcca ggtcgccctg cacagcgaca ccctgaatga 1380
atccggtttt gtggaagaca ccctcgccgc catcggcggg cgcaccatcc acaccttcca 1440
taccgaaggg gccggcggcg gccatgcgcc ggacatcatc accgcctgcg cccacccgaa 1500
cattttgccg tcgtccacca acccaacgct gccctacacc ctcaacacca tcaatgaaca 1560
tctcgatatg ctgatggtct gccaccatct ggacccggac atcgccgagg acgtggcctt 1620
tgccgagtcg cgcattcgcc gggaaaccat cgctgcggaa gacgtgctgc acgatctcgg 1680
cgccttctcg ctcacctcct ccgattcgca ggccatgggc cgcgtcgggg aagtgattct 1740
ccgcacctgg caggtggcgc atcgcatgaa ggtgcagcgc ggagcgctgg cggaggagac 1800
cggggataac gacaacttcc gcgtgaagcg ctacatcgcc aaatacacca tcaacccggc 1860
gctgacccac ggcatcgcac acgaagtcgg atccattgag gtgggtaagc tggctgacct 1920
cgtggtctgg tcaccagcct tcttcggcgt gaaaccggcc accgtgatca aaggcggcat 1980
gatcgccatc gcgccgatgg gcgatatcaa tgcctctatt ccgaccccgc agccggtgca 2040
ctaccgcccg atgtttggcg cgctgggcag cgcccgccat cactgccgcc tcaccttcct 2100
gtcgcaggcg gcggcagcca atggcgttgc cgagcggctg aacctgcgca gcgcgatcgc 2160
cgtggtgaaa ggctgccgta cggtgcagaa agccgacatg gtgcacaaca gtctgcagcc 2220

-continued

```
taacatcacc gtcgacgccc agacctatga ggtgcgggtg gatggcgaac ttatcaccag   2280

cgagccggca gacgttctgc cgatggcgca acgatatttt ctgttttaa               2329


<210> SEQ ID NO 9
<211> LENGTH: 2329
<212> TYPE: DNA
<213> ORGANISM: Klebsiella aerogenes

<400> SEQUENCE: 9

atggaactga ccccccgaga aaaagacaag ctgttgctgt ttaccgccgc gctggtggcg     60

gagcgtcgcc tggcccgcgg cctgaagctc aactatccgg agtccgtggc cctgatcagc    120

gcctttatta tggaaggcgc tcgggacggc aaaagcgtgg cctcgctgat ggaggaaggc    180

cgtcacgtcc tgacccgcga gcaggtgatg gagggcgtcc cggaaatgat cccggatatc    240

caggtcgaag ccaccttccc ggacggctcg aagctggtca ccgttcacaa cccgattatc    300

tgaggtagcg ccatgatccc cggtgaatat cacgttaagc ccggtcagat agccctgaat    360

accggccggg caacctgtcg cgtggtcgtt gagaaccacg gcgatcggcc gattcaggtc    420

ggttcgcact accatttcgc cgaggttaac ccggcgctga agttcgaccg tcagcaggcc    480

gccggctatc gcctgaatat cccggcgggc acggcggtac gctttgaacc cggccagaaa    540

cgcgaggtcg agctggtggc cttcgccggt caccgcgccg tcttcggctt ccgcggcgag    600

gtcatgggcc ctctggaggt aaacgatgag taatatttca cgccaggcct atgccgatat    660

gttcggcccc accgtcggcg acaaggtgcg cctggcagat accgagctgt ggatcgaggt    720

ggaggacgat ttgaccacct acggggaaga ggtcaaattc ggcggcggca aagtgatccg    780

cgacggcatg ggccagggac agatgctggc cgccgactgt gtcgacctgg tgctcaccaa    840

cgcgttgatc gtcgatcact gggggatcgt taaggccgat atcggcgtga aggacggccg    900

gatcttcgcc atcggcaaag ccggcaaccc cgacatccag cccaacgtca ccatccccat    960

cggcgctgcg acggaagtga tcgccgccga aggaaaaatt gtcaccgccg gcgggatcga   1020

tacccatatt cactggatct gtccgcagca ggcggaagag gcgctggtct ctggcgtgac   1080

caccatggtc ggcggcggca ccggcccggc cgcgggcacc catgccacca cctgcacccc   1140

gggcccgtgg tatatctcac gcatgctgca ggcggccgac agcctgccgg tcaatatcgg   1200

cctgctgggc aagggaaacg tttctcagcc ggatgccctg cgcgagcagg tggcggcagg   1260

cgttattggc ctgaagatcc atgaggactg gggcgccacc ccggcggcga tcgactgtgc   1320

gttaaccgtc gccgatgaaa tggacatcca ggtcgccctg cacagcgaca ccctgaatga   1380

atccggtttt gtggaagaca ccctcgccgc catcggcggg cgcaccatcc acaccttcca   1440

taccgaaggg gccggcggcg gccatgcgcc ggacatcatc accgcctgcg cccacccgaa   1500

cattttgccg tcgtccacca acccaacgct gccctacacc ctcaacacca tcaatgaaca   1560

tctcgatata ctgatggtct gccaccatct ggacccggac atcgccgagg acgtggcctt   1620

tgccgagtcg cgcattcgcc gggaaaccat cgctgcggaa gacgtgctgc acgatctcgg   1680

cgccttctcg ctcacctcct ccgattcgca ggccatgggc cgcgtcgggg aagtgattct   1740

ccgcacctgg caggtggcgc atcgcatgaa ggtgcagcgc ggagcgctgg cggaggagac   1800

cggggataac gacaacttcc gcgtgaagcg ctacatcgcc aaatacacca tcaacccggc   1860

gctgacccac ggcatcgcac acgaagtcgg atccattgag gtgggtaagc tggctgacct   1920

cgtggtctgg tcaccagcct tcttcggcgt gaaaccggcc accgtgatca aaggcggcat   1980

gatcgccatc gcgccgatgg gcgatatcaa tgcctctatt ccgacccgc agccggtgca   2040
```

-continued

```
ctaccgcccg atgtttggcg cgctgggcag cgcccgccat cactgccgcc tcaccttcct   2100

gtcgcaggcg gcggcagcca atggcgttgc cgagcggctg aacctgcgca gcgcgatcgc   2160

cgtggtgaaa ggctgccgta cggtgcagaa agccgacatg gtgcacaaca gtctgcagcc   2220

taacatcacc gtcgacgccc agacctatga ggtgcgggtg gatggcgaac ttatcaccag   2280

cgagccggca gacgttctgc cgatggcgca acgatatttt ctgttttaa               2329
```